United States Patent
Taylor et al.

(10) Patent No.: US 9,878,140 B2
(45) Date of Patent: Jan. 30, 2018

(54) ACCESS SEALING APPARATUS AND METHOD

(71) Applicant: Applied Medical Resources Corporation, Rancho Santa Margarita, CA (US)

(72) Inventors: Scott V. Taylor, Rancho Santa Margarita, CA (US); Henry Kahle, Corona, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 341 days.

(21) Appl. No.: 14/504,082

(22) Filed: Oct. 1, 2014

(65) Prior Publication Data

US 2015/0018626 A1 Jan. 15, 2015
US 2017/0340873 A9 Nov. 30, 2017

Related U.S. Application Data

(63) Continuation of application No. 13/417,950, filed on Mar. 12, 2012, now Pat. No. 8,870,904, which is a
(Continued)

(51) Int. Cl.
*A61B 17/34* (2006.01)
*A61M 39/06* (2006.01)
(Continued)

(52) U.S. Cl.
CPC ......... *A61M 39/06* (2013.01); *A61B 17/3423* (2013.01); *A61B 17/3462* (2013.01);
(Continued)

(58) Field of Classification Search
CPC ..... A61B 17/28; A61B 17/34; A61B 17/3428; A61B 17/3423; A61B 17/3462;
(Continued)

(56) References Cited

U.S. PATENT DOCUMENTS 558,364 A 4/1896 Doolittle
1,157,202 A 10/1915 Bates et al.
(Continued)

FOREIGN PATENT DOCUMENTS

DE 26 05 148 A1 8/1977
DE 33 36 279 C2 1/1986
(Continued)

OTHER PUBLICATIONS

U.S. Appl. No. 10/381,220, filed Mar. 20, 2003; Title: Surgical Access Apparatus and Method, now U.S. Pat. No. 7,473,221 issued Jan. 6, 2009.
(Continued)

*Primary Examiner* — Tuan V Nguyen
(74) *Attorney, Agent, or Firm* — Patrick Y. Ikehara

(57) ABSTRACT

A surgical access device includes a seal housing and a roller disposed in the housing and defining a working channel. The roller may be stationary or moveable within the seal housing to form both a zero seal in the absence of an instrument, and an instrument seal in the presence of an instrument. Rotation of the roller is contemplated and low-friction surfaces are discussed to reduce instrument insertion forces. Multiple rollers, wiper elements, low-friction braid, pivoting elements and idler rollers are contemplated. The rollers will typically be formed of a gel material in order to facilitate the desired compliance, stretchability and elongation desired.

17 Claims, 19 Drawing Sheets

Related U.S. Application Data continuation of application No. 12/791,607, filed on Jun. 1, 2010, now Pat. No. 8,157,835, which is a continuation of application No. 10/776,387, filed on Feb. 10, 2004, now Pat. No. 7,727,255, which is a continuation of application No. PCT/US02/15696, filed on May 14, 2002.

(60) Provisional application No. 60/312,683, filed on Aug. 14, 2001.

(51) Int. Cl.
 A61B 17/00 (2006.01)
 A61B 17/22 (2006.01)

(52) U.S. Cl.
 CPC .............. *A61B 17/3498* (2013.01); *A61B 2017/00469* (2013.01); *A61B 2017/22067* (2013.01); *A61B 2017/3441* (2013.01); *A61M 2039/0626* (2013.01); *A61M 2039/0673* (2013.01)

(58) Field of Classification Search
 CPC ...... A61B 17/3498; A61B 2017/00469; A61B 2017/3441; A61B 2017/22067; A61M 2039/0626; A61M 2039/0673; A61M 39/06
 See application file for complete search history.

(56) References Cited

U.S. PATENT DOCUMENTS

| | | |
|---|---|---|
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,729,027 A | 4/1973 | Bare |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,083,370 A | 4/1978 | Taylor |
| 4,096,853 A | 6/1978 | Weigand |
| 4,112,932 A | 9/1978 | Chiulli |
| 4,117,847 A | 10/1978 | Clayton |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Banjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |

(56) References Cited

U.S. PATENT DOCUMENTS

| | | |
|---|---|---|
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,201,714 A * | 4/1993 | Gentelia ............ A61B 17/3462 251/149.2 |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Blake, III et al. |
| 5,242,409 A | 9/1993 | Buelna |
| 5,242,412 A | 9/1993 | Blake, III et al. |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Soya et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Durdal et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |

(56) References Cited

U.S. PATENT DOCUMENTS

| | | |
|---|---|---|
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis |
| 5,662,615 A | 9/1997 | Blake, III |
| 5,672,168 A | 9/1997 | de la Torre et al. |
| 5,681,341 A | 10/1997 | Lunsford et al. |
| 5,683,378 A | 11/1997 | Christy |
| 5,685,854 A | 11/1997 | Green et al. |
| 5,685,857 A | 11/1997 | Negus et al. |
| 5,697,914 A | 12/1997 | Brimhall |
| 5,707,703 A | 1/1998 | Rothrum et al. |
| 5,709,664 A | 1/1998 | Vandenbroek et al. |
| 5,713,858 A | 2/1998 | Heruth et al. |
| 5,713,869 A | 2/1998 | Morejon |
| 5,720,730 A | 2/1998 | Blake, III |
| 5,725,536 A | 3/1998 | Oberlin et al. |
| 5,728,103 A | 3/1998 | Picha et al. |
| 5,730,748 A | 3/1998 | Fogarty et al. |
| 5,735,791 A | 4/1998 | Alexander et al. |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,760,117 A | 6/1998 | Chen |
| 5,769,783 A | 6/1998 | Fowler |
| 5,782,812 A | 7/1998 | Hart et al. |
| 5,782,817 A | 7/1998 | Franzel et al. |
| 5,782,859 A | 7/1998 | Nicholas et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,807,350 A | 9/1998 | Diaz |
| 5,810,712 A | 9/1998 | Dunn |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom et al. |
| 5,819,375 A | 10/1998 | Kastner |
| 5,820,555 A | 10/1998 | Watkins et al. |
| 5,820,600 A | 10/1998 | Carlson et al. |
| 5,830,191 A | 11/1998 | Hildwein et al. |
| 5,832,925 A | 11/1998 | Rothrum |
| 5,836,871 A | 11/1998 | Wallace et al. |
| 5,841,298 A | 11/1998 | Huang |
| 5,842,971 A | 12/1998 | Yoon |
| 5,848,992 A | 12/1998 | Hart et al. |
| 5,853,395 A | 12/1998 | Crook et al. |
| 5,853,417 A | 12/1998 | Fogarty et al. |
| 5,857,461 A | 1/1999 | Levitsky et al. |
| 5,860,995 A | 1/1999 | Berkelaar |
| 5,865,728 A | 2/1999 | Moll et al. |
| 5,865,729 A | 2/1999 | Meehan et al. |
| 5,865,807 A | 2/1999 | Blake, III |
| 5,865,817 A | 2/1999 | Moenning et al. |
| 5,871,474 A | 2/1999 | Hermann et al. |
| 5,876,413 A | 3/1999 | Fogarty et al. |
| 5,879,368 A | 3/1999 | Hoskin et al. |
| 5,882,344 A | 3/1999 | Strouder, Jr. |
| 5,884,639 A | 3/1999 | Chen |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,913,847 A | 6/1999 | Yoon |
| 5,916,198 A | 6/1999 | Dillow |
| 5,916,232 A | 6/1999 | Hart |
| 5,919,476 A | 7/1999 | Fischer et al. |
| 5,931,832 A | 8/1999 | Jensen |
| 5,947,922 A | 9/1999 | MacLeod |
| 5,951,467 A | 9/1999 | Picha et al. |
| 5,951,588 A | 9/1999 | Moenning |
| 5,957,888 A | 9/1999 | Hinchiffe et al. |
| 5,957,913 A | 9/1999 | de la Torre et al. |
| 5,962,572 A | 10/1999 | Chen |
| 5,964,781 A | 10/1999 | Mollenauer et al. |
| 5,976,174 A | 11/1999 | Ruiz |
| 5,989,232 A | 11/1999 | Yoon |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,994,450 A | 11/1999 | Pearce |
| 5,997,515 A | 12/1999 | de la Torre et al. |
| 6,004,303 A | 12/1999 | Peterson |
| 6,010,494 A | 1/2000 | Schafer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Ben Nun |
| 6,048,309 A | 4/2000 | Flom et al. |

(56) References Cited

U.S. PATENT DOCUMENTS

| | | |
|---|---|---|
| 6,050,871 A | 4/2000 | Chen |
| 6,053,934 A | 4/2000 | Andrews et al. |
| 6,059,816 A | 5/2000 | Moenning |
| 6,066,117 A | 5/2000 | Fox et al. |
| 6,068,639 A | 5/2000 | Fogarty et al. |
| 6,076,560 A | 6/2000 | Stahle et al. |
| 6,077,288 A | 6/2000 | Shimomura |
| 6,086,603 A | 7/2000 | Termin et al. |
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 | 7/2001 | Dennis et al. |
| 6,264,604 B1 | 7/2001 | Kieturakis et al. |
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West |
| 6,325,384 B1 | 12/2001 | Berry, Sr. et al. |
| 6,346,074 B1 | 2/2002 | Roth |
| 6,371,968 B1 | 4/2002 | Kogasaka et al. |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 * | 4/2003 | Bimbo ............... A61B 17/3423 604/167.03 |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Liu et al. |
| 7,105,009 B2 | 9/2006 | Johnson |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |

(56) References Cited

U.S. PATENT DOCUMENTS

| | | | |
|---|---|---|---|
| 7,163,510 B2 | 1/2007 | Kahle et al. | |
| 7,192,436 B2 | 3/2007 | Sing et al. | |
| 7,193,002 B2 | 3/2007 | Chen | |
| 7,195,590 B2 | 3/2007 | Butler et al. | |
| 7,214,185 B1 | 5/2007 | Rosney et al. | |
| 7,217,277 B2 | 5/2007 | Parihar et al. | |
| 7,222,380 B2 | 5/2007 | Chen | |
| 7,223,257 B2 | 5/2007 | Shubayev et al. | |
| 7,223,278 B2 | 5/2007 | Davison et al. | |
| 7,226,484 B2 | 6/2007 | Chen | |
| 7,235,062 B2 | 6/2007 | Brustad | |
| 7,235,084 B2 | 6/2007 | Skakoon et al. | |
| 7,238,154 B2 | 7/2007 | Ewers et al. | |
| 7,244,244 B2 | 7/2007 | Racenet et al. | |
| 7,276,075 B1 | 10/2007 | Callas et al. | |
| 7,290,367 B2 | 11/2007 | Chen | |
| 7,294,103 B2 | 11/2007 | Bertolero et al. | |
| 7,297,106 B2 | 11/2007 | Yamada et al. | |
| 7,300,399 B2 | 11/2007 | Bonadio et al. | |
| 7,316,699 B2 | 1/2008 | McFarlane | |
| 7,331,940 B2 | 2/2008 | Sommerich | |
| 7,338,473 B2 | 3/2008 | Campbell et al. | |
| 7,344,541 B2 | 3/2008 | Piskun | |
| 7,344,546 B2 | 3/2008 | Wulfman et al. | |
| 7,344,568 B2 | 3/2008 | Chen | |
| 7,377,898 B2 | 5/2008 | Ewers et al. | |
| 7,390,317 B2 | 6/2008 | Taylor et al. | |
| 7,393,322 B2 | 7/2008 | Wenchell | |
| 7,412,977 B2 | 8/2008 | Fields et al. | |
| 7,445,597 B2 | 11/2008 | Butler et al. | |
| 7,473,221 B2 | 1/2009 | Ewers et al. | |
| 7,481,765 B2 | 1/2009 | Ewers et al. | |
| 7,537,564 B2 | 5/2009 | Bonadio et al. | |
| 7,540,839 B2 | 6/2009 | Butler et al. | |
| 7,559,893 B2 | 7/2009 | Bonadio et al. | |
| 7,578,832 B2 | 8/2009 | Johnson | |
| 7,645,232 B2 | 1/2010 | Shluzas | |
| 7,650,887 B2 | 1/2010 | Nguyen et al. | |
| 7,661,164 B2 | 2/2010 | Chen | |
| 7,704,207 B2 | 4/2010 | Albrecht et al. | |
| 7,717,847 B2 | 5/2010 | Smith | |
| 7,727,146 B2 | 6/2010 | Albrecht et al. | |
| 7,727,255 B2 | 6/2010 | Taylor et al. | |
| 7,736,306 B2 | 6/2010 | Brustad et al. | |
| 7,749,415 B2 | 7/2010 | Brustad et al. | |
| 7,753,901 B2 | 7/2010 | Piskun et al. | |
| 7,758,500 B2 | 7/2010 | Boyd et al. | |
| 7,766,824 B2 | 8/2010 | Jensen et al. | |
| 7,811,251 B2 | 10/2010 | Wenchell et al. | |
| 7,815,567 B2 | 10/2010 | Albrecht et al. | |
| 7,837,612 B2 | 11/2010 | Gill et al. | |
| 7,841,765 B2 | 11/2010 | Keller | |
| 7,850,667 B2 | 12/2010 | Gresham | |
| 7,867,164 B2 | 1/2011 | Butler et al. | |
| 7,878,974 B2 | 2/2011 | Brustad et al. | |
| 7,896,889 B2 | 3/2011 | Mazzocchi et al. | |
| 7,909,760 B2 | 3/2011 | Albrecht et al. | |
| 7,930,782 B2 | 4/2011 | Chen | |
| 8,157,835 B2 * | 4/2012 | Taylor | A61B 17/3423 604/167.01 |
| RE43,379 E * | 5/2012 | Suzuki | G10H 1/0041 84/600 |
| 8,870,904 B2 * | 10/2014 | Taylor | A61B 17/3462 604/167.01 |
| 2001/0037053 A1 | 11/2001 | Bonadio et al. | |
| 2001/0047188 A1 | 11/2001 | Bonadio et al. | |
| 2002/0002324 A1 | 1/2002 | McManus | |
| 2002/0010389 A1 | 1/2002 | Butler et al. | |
| 2002/0013542 A1 | 1/2002 | Bonadio et al. | |
| 2002/0016607 A1 | 2/2002 | Bonadio et al. | |
| 2002/0026230 A1 | 2/2002 | Moll et al. | |
| 2002/0038077 A1 | 3/2002 | de la Torre et al. | |
| 2002/0072762 A1 | 6/2002 | Bonadio et al. | |
| 2002/0111536 A1 | 8/2002 | Cuschieri et al. | |
| 2003/0004253 A1 | 1/2003 | Chen | |
| 2003/0014076 A1 | 1/2003 | Mollenauer et al. |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlbert et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkier, II et al. |
| 2005/0090713 A1 | 4/2005 | Gozales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker et al. |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |

(56) References Cited

U.S. PATENT DOCUMENTS

| | | |
|---|---|---|
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0088204 A1 | 4/2007 | Albrecht |
| 2007/0093695 A1 | 4/2007 | Bonadio et al. |
| 2007/0118175 A1 | 5/2007 | Butler et al. |
| 2007/0149859 A1 | 6/2007 | Albrecht |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0270752 A1 | 11/2007 | Labombard |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht |
| 2008/0281162 A1 | 11/2008 | Albrecht |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0182282 A1 | 7/2009 | Okihisa |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegel et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |
| 2010/0286484 A1 | 11/2010 | Stellon et al. |
| 2010/0298646 A1 | 11/2010 | Stellon et al. |
| 2011/0021877 A1 | 1/2011 | Fortier et al. |
| 2011/0028891 A1 | 2/2011 | Okoniewski |
| 2011/0034935 A1 | 2/2011 | Kleyman |
| 2011/0034946 A1 | 2/2011 | Kleyman |
| 2011/0034947 A1 | 2/2011 | Kleyman |
| 2011/0071462 A1 | 3/2011 | Ewers et al. |
| 2011/0071463 A1 | 3/2011 | Ewers et al. |
| 2012/0095297 A1 | 4/2012 | Dang et al. |

FOREIGN PATENT DOCUMENTS

| | | |
|---|---|---|
| DE | 37 39 532 | 12/1988 |
| DE | 37 37 121 | 5/1989 |
| DE | 296 00 939 | 6/1996 |
| DE | 19828009 | 12/1999 |
| EP | 0 113 520 | 7/1984 |
| EP | 0 142 262 | 5/1985 |
| EP | 0 517 248 | 12/1992 |
| EP | 0 537 768 | 4/1993 |
| EP | 0 807 416 | 11/1997 |
| EP | 0 849 517 | 6/1998 |
| EP | 0950376 | 10/1999 |
| EP | 1 118 657 | 7/2001 |
| EP | 1 125 552 | 8/2001 |
| EP | 1 312 318 | 5/2003 |
| EP | 1 407 715 | 4/2004 |
| EP | 2 044 889 | 4/2009 |
| EP | 2 272 450 A2 | 1/2011 |
| EP | 2 340 792 | 7/2011 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| RU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |

(56) References Cited

FOREIGN PATENT DOCUMENTS

| | | |
|---|---|---|
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/26559 | 4/2001 |
| WO | WO 01/45568 | 6/2001 |
| WO | WO 01/045568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO 03/034908 | 5/2003 |
| WO | WO 03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2007/044849 | 4/2007 |
| WO | WO 2008/015566 | 2/2008 |
| WO | WO 2008/093313 | 8/2008 |
| WO | WO 2008/121294 | 10/2008 |
| WO | WO 2010/045253 | 4/2010 |
| WO | WO 2010/082722 | 7/2010 |
| WO | WO 2010/104259 | 9/2010 |

OTHER PUBLICATIONS

U.S. Appl. No. 10/436,522, filed May 13, 2003; Title: Laparoscopic Illumination Apparatus and Method, now U.S. Pat. No. 6,939,296 issued Sep. 6, 2005.
U.S. Appl. No. 10/399,209, filed Aug. 22, 2003; Title: Wound Retraction Apparatus and Method, now U.S. Pat. No. 6,958,037 issued Oct. 25, 2005.
U.S. Appl. No. 11/218,412, filed Sep. 1, 2005; Title: Wound Retraction Apparatus and Method, now U.S. Pat. No. 7,238,154 issued Jul. 3, 2007.
U.S. Appl. No. 10/399,057, filed Apr. 11, 2003; Title: Sealed Surgical Access Device, now U.S. Pat. No. 7,052,454 issued May 30, 2006.
U.S. Appl. No. 10/666,579, filed Sep. 17, 2003; Title: Surgical Instrument Access Device, now U.S. Pat. No. 7,163,510 issued Jan. 16, 2007.
U.S. Appl. No. 10/052,297, filed Jan. 18, 2002; Title: Hand Access Port Device, now U.S. Pat. No. 6,908,430 issued Jun. 21, 2005.
U.S. Appl. No. 08/015,765, filed Feb. 10, 1993; Title: Gas-Tight Seal Accomodating Surgical Instruments With a Wide Range of Diameters, now U.S. Pat. No. 5,407,433 issued Apr. 18, 1995.
U.S. Appl. No. 08/040,373, filed Mar. 30, 1993; Title: Gas-Tight Seal Accomodating Surgical Instruments With a Wide Range of Diameters, now U.S. Pat. No. 5,411,483 issued May 2, 1995.
U.S. Appl. No. 10/902,756, filed Jul. 29, 2004; Title: Hand Access Port Device, now abandoned.
U.S. Appl. No. 10/802,125, filed Mar. 15, 2004; Title: Surgical Guide Valve, now abandoned.
U.S. Appl. No. 10/516,198, filed Nov. 30, 2004; Title: Wound Retractor, now U.S. Pat. No. 7,650,887 issued Jan. 26, 2010.
U.S. Appl. No. 10/927,551, filed Aug. 25, 2004; Title: Surgical Access System, now abandoned.
U.S. Appl. No. 11/244,647, filed Oct. 5, 2005; Title: Surgical Access Apparatus and Method, now U.S. Pat. No. 7,481,765 issued Jan. 27, 2009.
U.S. Appl. No. 11/548,746, filed Oct. 12, 2006; Title: Method of Making a Hand Access Laparoscopic Device, now U.S. Pat. No. 7,749,415 issued Jul. 6, 2010.
U.S. Appl. No. 11/548,765, filed Oct. 12, 2006; Title: Split Hoop Wound Retractor, now U.S. Pat. No. 7,815,567 issued Oct. 26, 2010.
U.S. Appl. No. 11/548,767, filed Oct. 12, 2006; Title: Circular Surgical Retractor now U.S. Pat. No. 7,704,207 issued Apr. 27, 2010.
U.S. Appl. No. 11/548,781, filed Oct. 12, 2006; Title: Wound Retractor With Gel Cap, now U.S. Pat. No. 7,727,146 issued Jun. 1, 2010.
U.S. Appl. No. 11/548,955, filed Oct. 12, 2006; Title: Hand Access Laparoscopic Device, now U.S. Pat. No. 7,736,306 issued Jun. 15, 2010.
U.S. Appl. No. 11/755,305, filed May 30, 2007; Title: Wound Retraction Apparatus and Method, now U.S. Pat. No. 7,377,898 issued May 27, 2008.
U.S. Appl. No. 11/548,758, filed Oct. 12, 2007; Title: Split Hoop Wound Retractor With Gel Pad, now U.S. Pat. No. 7,909,760 issued Mar. 22, 2011.
U.S. Appl. No. 12/693,242, filed Jan. 1, 2010; Title: Wound Retractor, now U.S. Pat. No. 7,913,697 issued Mar. 29, 2011.
U.S. Appl. No. 12/768,328, filed Apr. 27, 2010; Title: Circular Surgical Retractor, now U.S. Pat. No. 7,892,172 issued Feb. 22, 2011.
U.S. Appl. No. 12/791,666, filed Jun. 1, 2010; Title: Wound Retractor With Gel Cap, now U.S. Pat. No. 7,883,461 issued Feb. 8, 2011.
U.S. Appl. No. 12/815,986, filed Jun. 15, 2010; Title: Hand Access Laparoscopic Device, now U.S. Pat. No. 7,878,974 issued Feb. 1, 2011.
U.S. Appl. No. 10/695,295, filed Oct. 28, 2003; Title: Surgical Gel Seal.
U.S. Appl. No. 11/132,741, filed May 18, 2005; Title: Gas-Tight Seal Accomodating Surgical Instruments With a Wide Range of Diameters.
U.S. Appl. No. 11/245,709, filed Oct. 7, 2005; Title: Surgical Access System.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.

(56) References Cited

OTHER PUBLICATIONS

U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011; Title: Hand Access Laparoscopic Device.
U.S. Appl. No. 13/008,728, filed Jan. 18, 2011; Title: Wound Retractor With Gel Cap.
U.S. Appl. No. 13/023,334, filed Feb. 8, 2011; Title: Circular Surgical Retractor.
U.S. Appl. No. 13/031,892, filed Feb. 22, 2011; Title: Wound Retractor.
U.S. Appl. No. 13/050,042, filed Mar. 17, 2011; Title: Split Hoop Wound Retractor With Gel Pad.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc., dated 1999.
European Patent Office, European Search Report for European Application No. EP 10 18 4681, entitled "Wound Retraction Apparatus and Method", dated Nov. 22, 2010.
European Patent Office, European Search Report for European Application No. EP 10 18 4608, entitled "Wound Retraction Apparatus and Method", dated Nov. 22, 2010.
European Patent Office, European Search Report for European Application No. EP 10 18 4648, entitled "Wound Retraction Apparatus and Method", dated Nov. 22, 2010.
European Patent Office, European Search Report for European Application No. EP 10 18 4731, entitled "Wound Retraction Apparatus and Method", dated Nov. 22, 2010.
European Patent Office, European Search Report for European Application No. EP 10 18 4661, entitled "Wound Retraction Apparatus and Method", dated Nov. 22, 2010.
European Patent Office, European Search Report for European Application No. EP 10 18 4677, entitled "Wound Retraction Apparatus and Method", dated Nov. 22, 2010.
European Patent Office, European Search Report for European Application No. EP 10 18 9325, entitled "Split Hoop Wound Retractor", dated Dec. 14, 2010.
European Patent Office, European Search Report for European Application No. EP 10 18 9327, entitled "Split Hoop Wound Retractor", dated Dec. 14, 2010.
European Patent Office, European Search Report for European Application No. EP 10 18 9328, entitled "Split Hoop Wound Retractor", dated Dec. 15, 2010.
European Patent Office, European Search Report for European Application No. EP 04 00 2888, entitled "Hand Access Port Device", dated Sep. 10, 2004.
European Patent Office, European Search Report for European Application No. EP 04 00 2889, entitled "Hand Access Port Device", dated Sep. 13, 2004.
European Patent Office, International Search Report and The Written Opinion of the International Searching Authority for International Application No. PCT/US2006/040154, dated Jan. 30, 2007.
European Patent Office, International Search Report and The Written Opinion of the International Searching Authority for International Application No. PCT/US2006/040073, dated Jan. 26, 2007.
European Patent Office, International Search Report and The Written Opinion of the International Searching Authority for International Application No. PCT/US2006/039905, dated Jan. 17, 2007.
European Patent Office, International Search Report and The Written Opinion of the International Searching Authority for International Application No. PCT/US2006/039883, dated Jan. 31, 2007.
European Patent Office, International Search Report and The Written Opinion of the International Searching Authority for International Application No. PCT/US2006/039800, dated Apr. 16, 2007.
European Patent Office, International Search Report and The Written Opinion of the International Searching Authority for International Application No. PCT/US2006/039799, dated Mar. 27, 2007.
European Patent Office, European Search Report for European Application No. EP 08253236 dated Feb. 10, 2009.
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484, dated Nov. 12, 2004.
International Searching Authority/US, International Search Report and the Written Opinion of the International Searching Authority for International Application No. PCT/US01/29682, dated Jun. 14, 2002.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan, dated 1992.
The International Bureau of WIPO, International Preliminary Report on Patentability for International Application No. PCT/US2004/028250, dated Aug. 29, 2006.
The International Bureau of WIPO, International Preliminary Report on Patentability for International Application No. PCT/US2006/039799, dated Apr. 16, 2008.
The International Bureau of WIPO, International Preliminary Report on Patentability for International Application No. PCT/US2006/039800 dated Apr. 16, 2008.

(56) References Cited

OTHER PUBLICATIONS

Yamazaki, et al., Diurnal Changes in the Composition of Abomasal Digesta in Fasted and Fed Sheep, The Tohoki Journal of Agricultural Research, Mar. 1987, vol. 37, No. 34, pp. 49-58.
Kagaya, "Laparascopic cholecystecomy via two ports, using the Twin-Port" system, J. Hepatobiliary Pancreat Surg (2001) 8:76-80, dated Feb. 20, 2001.
Declaration of John R. Brustad dated Dec. 10, 2009, submitted in U.S. Appl. No. 11/548,955, including Appendices A-D regarding product sales brochures and production drawings from 2001 and 2005.
InternationalSearch Report and Written Opinion for PCT/IE2005/000113, dated Feb. 22, 2006.
International Searching Authority—US, International Search Report and Written Opinion of the International Searching Authority for International Application No. PCT/US04/25511, dated Nov. 7, 2007.
International Bureau of WIPO, International Report on Patentability for International Application No. PCT/US04/25511, dated Dec. 6, 2007.
International Search Report and Written Opinion for PCT/IE2007/000050 dated Aug. 13, 2007.
The International Searching Authority, The International Search Report and Written Opinion of the International Searching Authority for International Application No. PCT/US08/63445, dated Sep. 29, 2008.
The International Searching Authority, The International Search Report and Written Opinion of the International Searching Authority for International Application No. PCT/US08/063463 dated Sep. 10, 2008.

The International Bureau of WIPO, International Preliminary Report on Patentability for International Application No. PCT/US2008/063463, entitled "Surgical Retractor", dated Nov. 17, 2009.
The International Bureau of WIPO, International Preliminary Report on Patentability for International Application No. PCT/US08/63445, entitled "Surgical Retractor with Gel Pad", dated Nov. 17, 2009.
International Searching Authority—European Patent Office, The International Search Report and Written Opinion for International Application No. PCT/US2011/054266, dated Feb. 9, 2012.
European Patent Office, European Search Report for European Patent No. 11172709.5, dated Aug. 16, 2011.
European Patent Office, European Search Report for European Patent No. 11172706.1, dated Aug. 16, 2011.
European Patent Office, European Search Report for European Patent No. 12151288, dated Feb. 10, 2012.
European Patent Office, European Search Report for European Patent No. 08755332, dated Apr. 18, 2012.
European Patent Office, Supplementary European Search Report for European Patent Application No. 08755322, dated Apr. 18, 2012.
European Patent Office, Supplementary European Search Report for European Patent Application No. 08755336, dated Jun. 15, 2012.
Harold W. Harrower, M.D., Isolation of Incisions into Body Cavities, The American Journal of Surgery, vol. 116, pp. 824-826, Dec. 1968.
International Searching Authority—European Patent Office, The International Search Report and Written Opinion for International Application No. PCT/US2013/037213, dated Jul. 3, 2013.

* cited by examiner

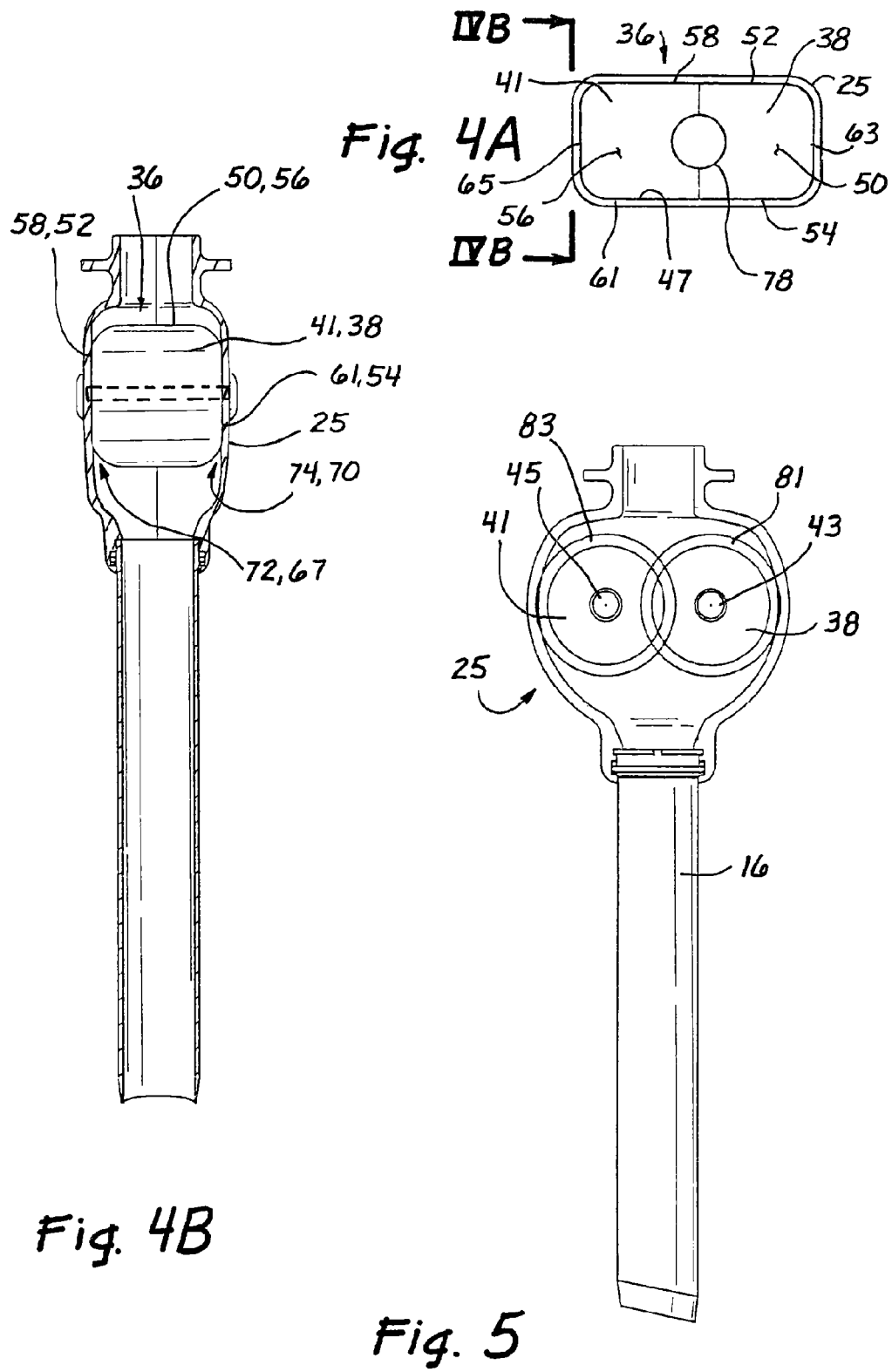

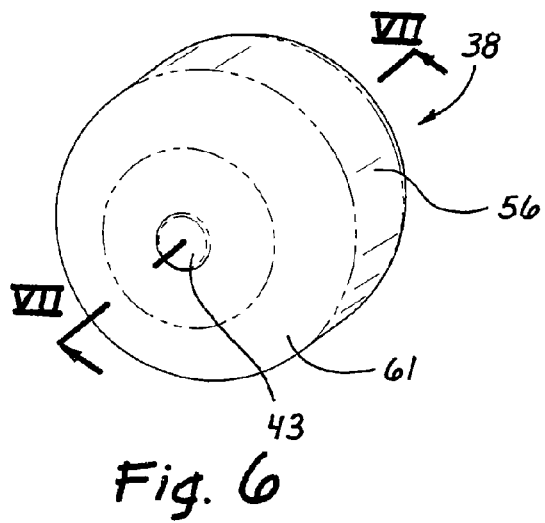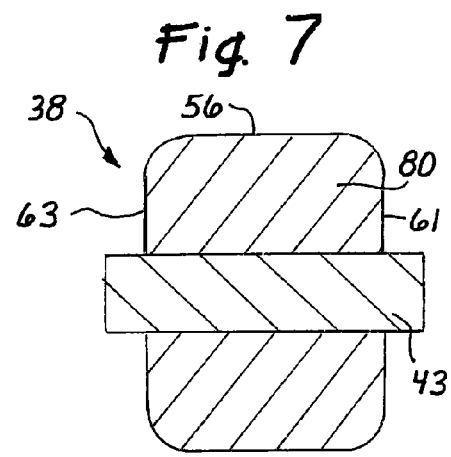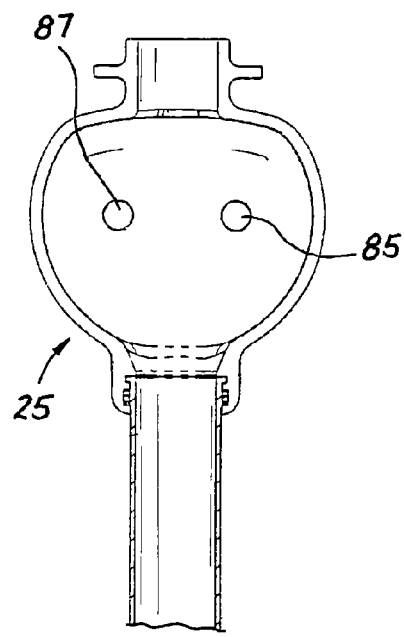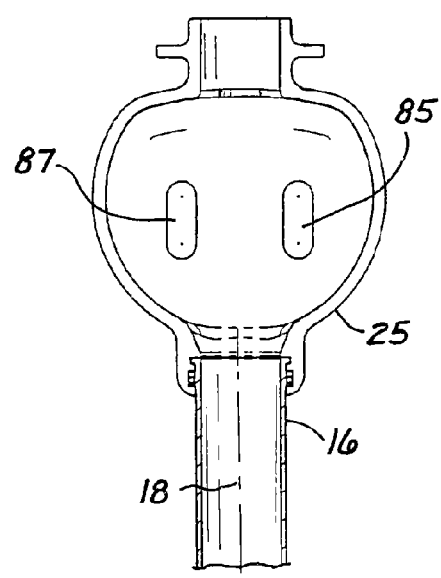

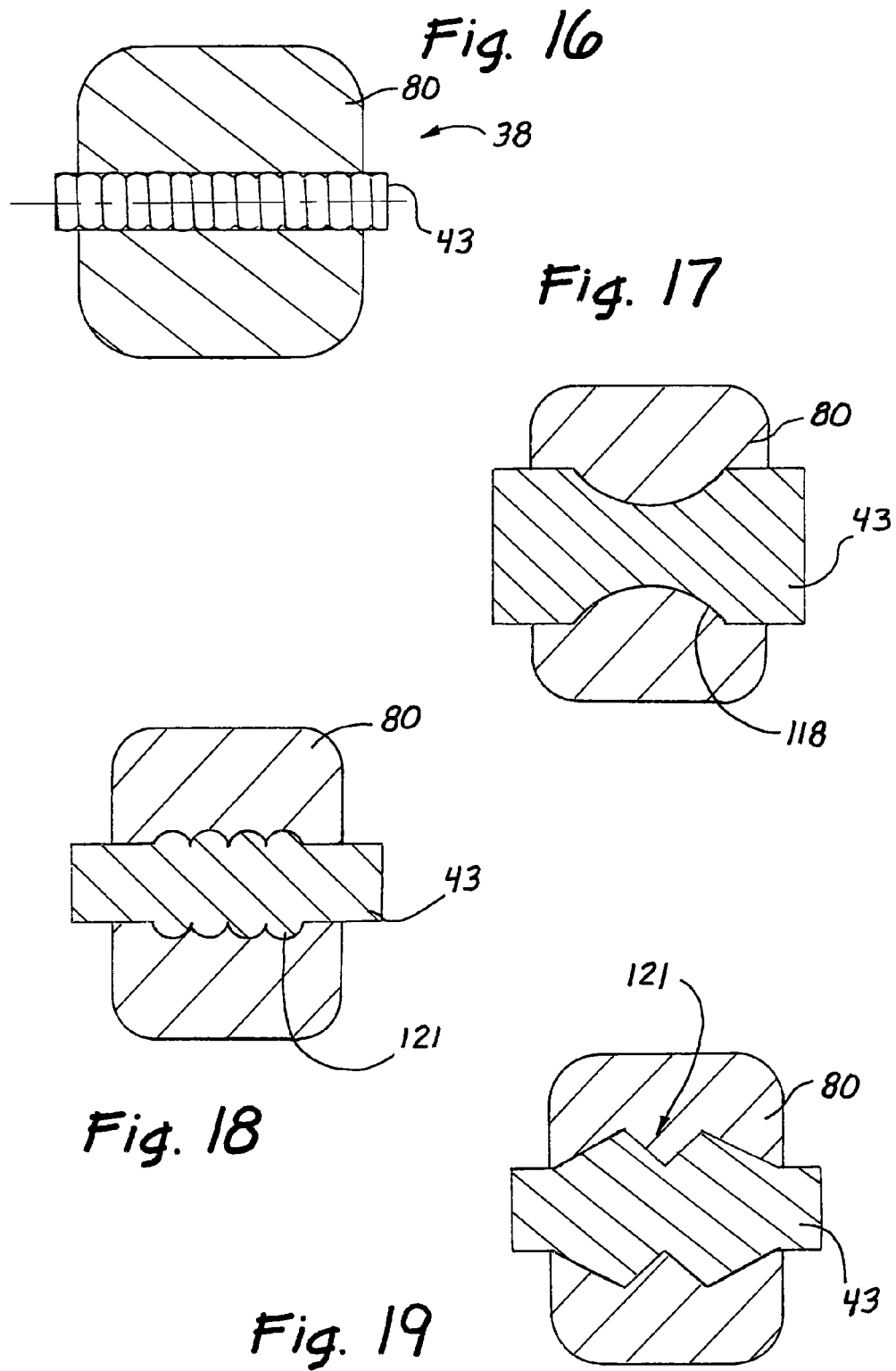

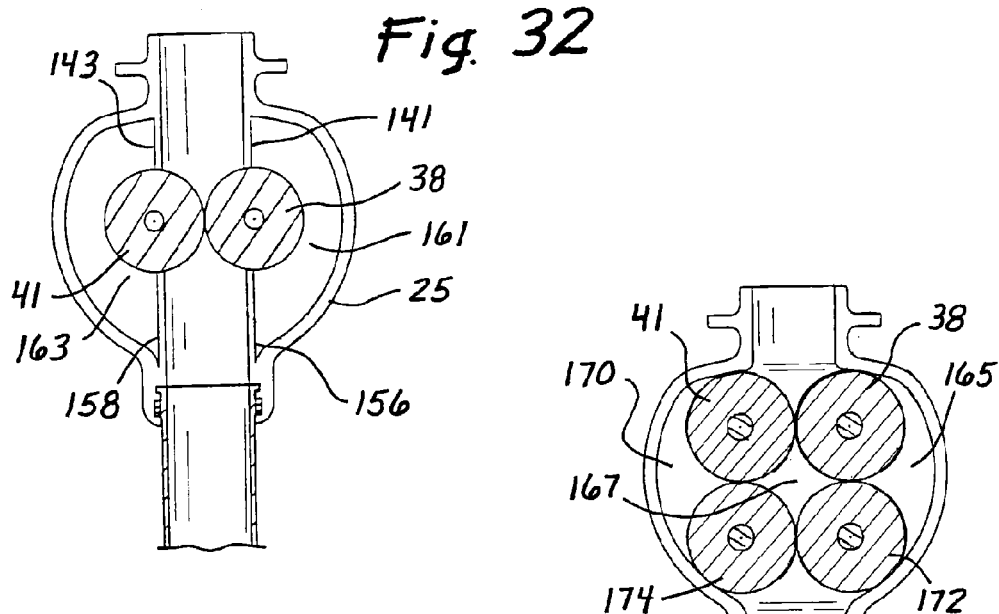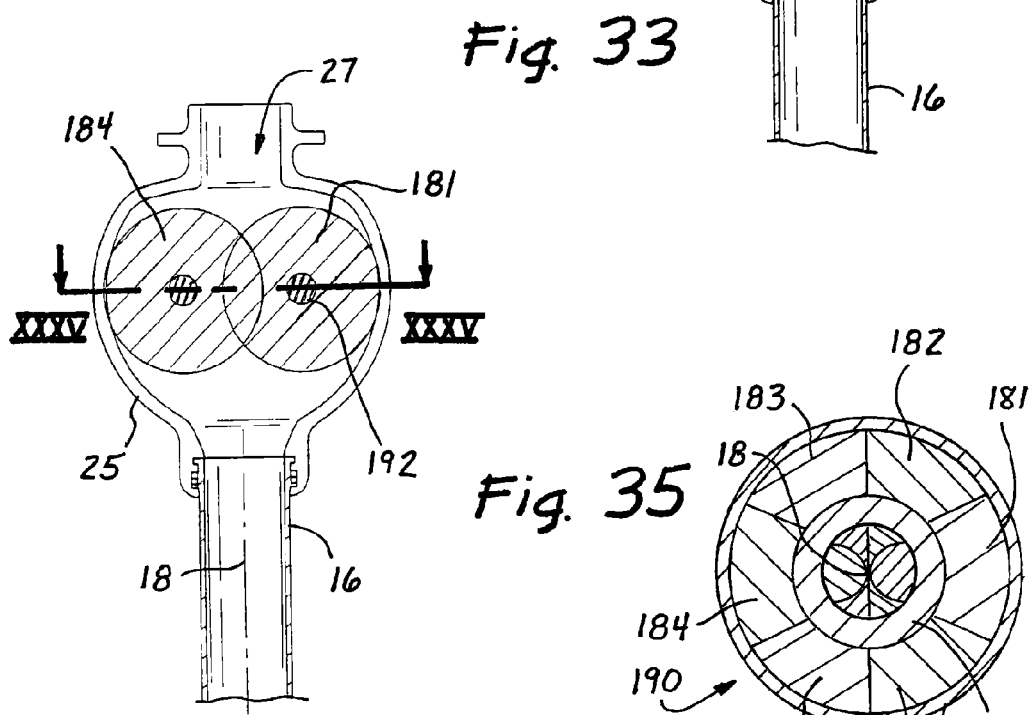

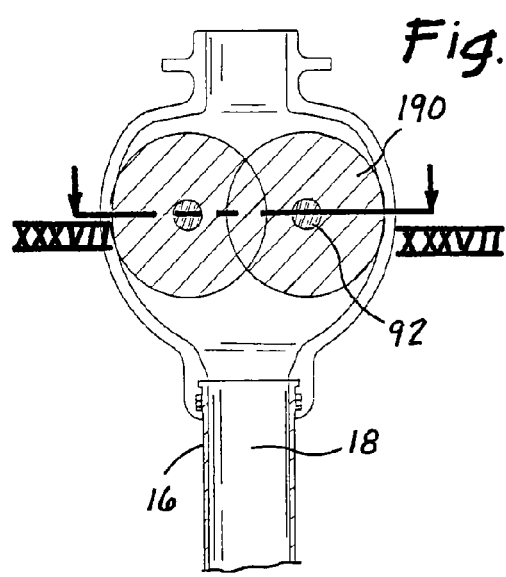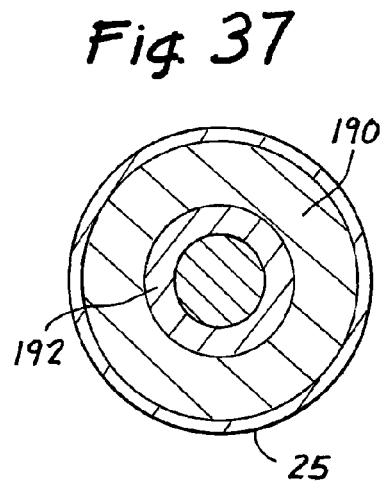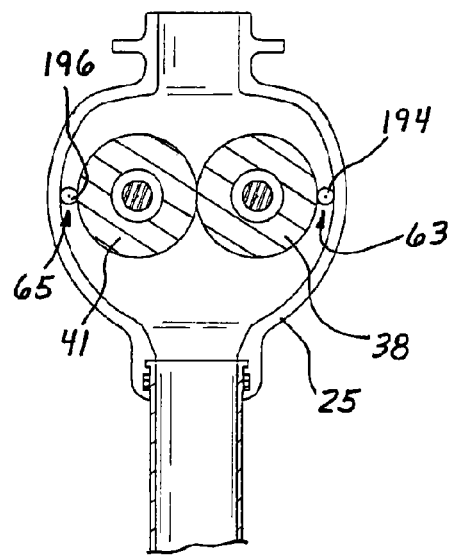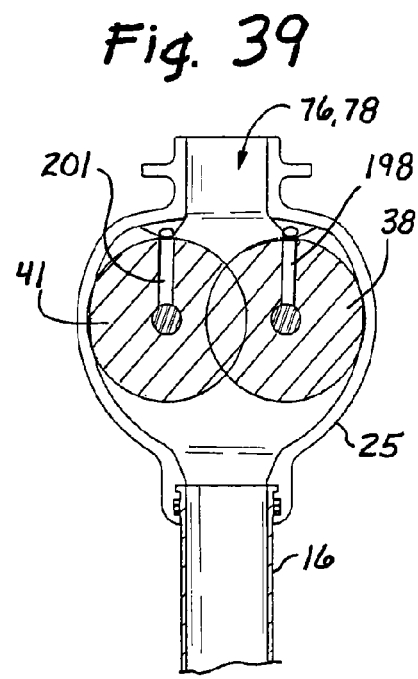

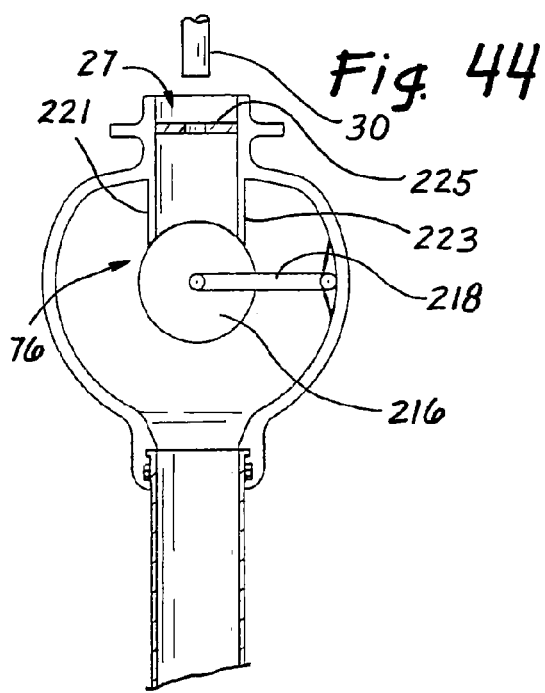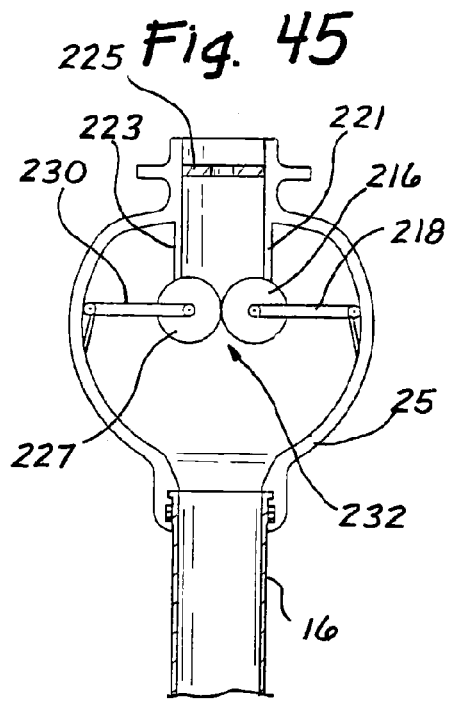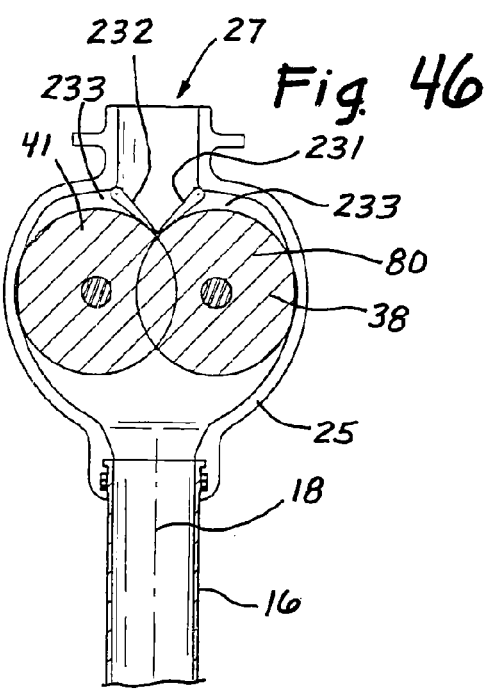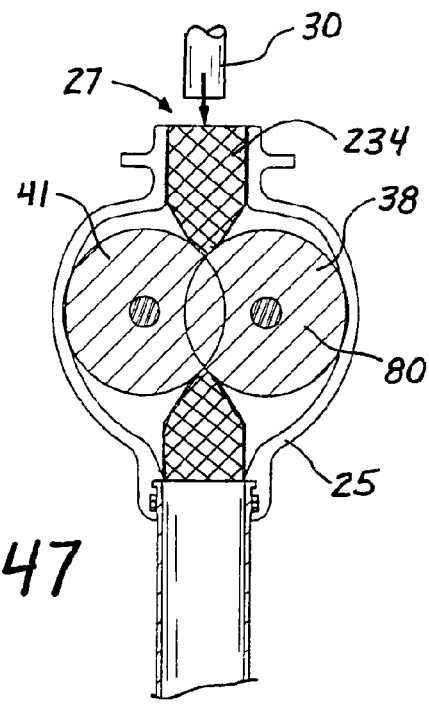

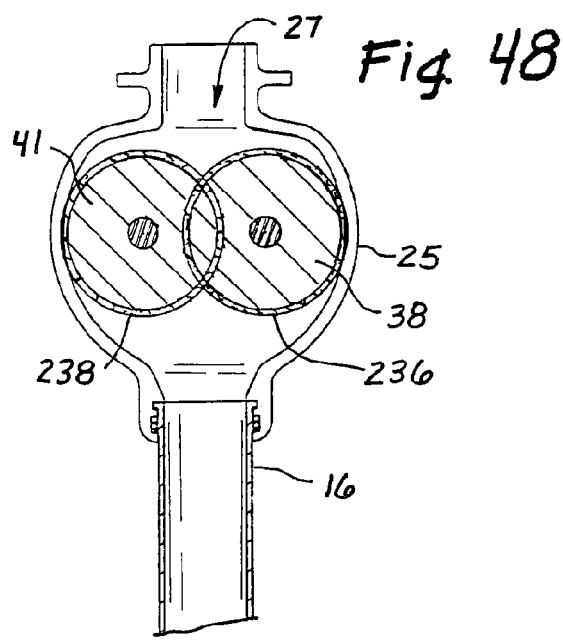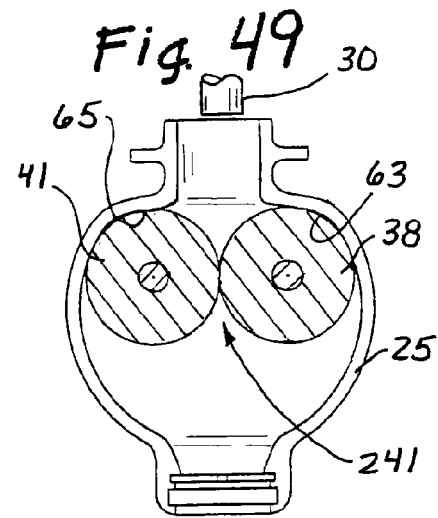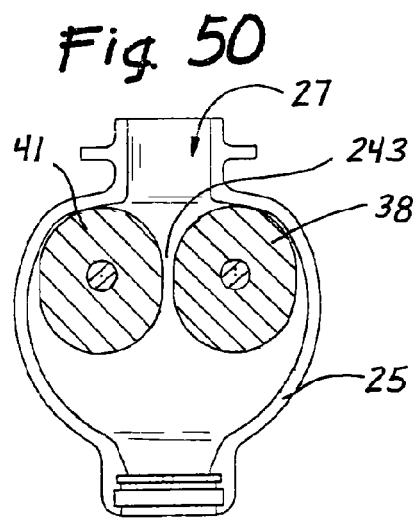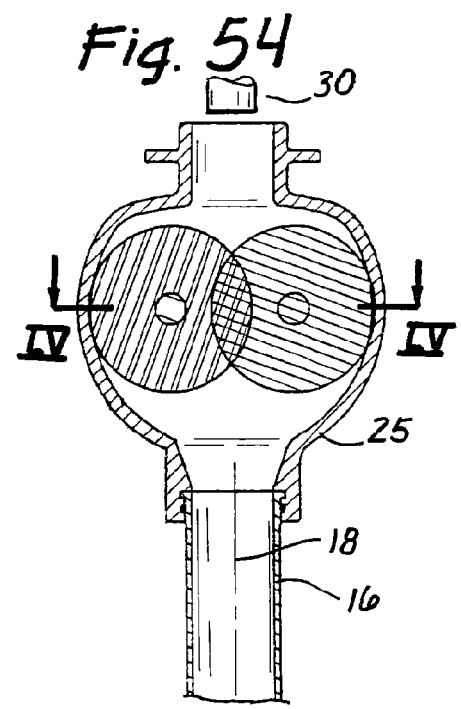

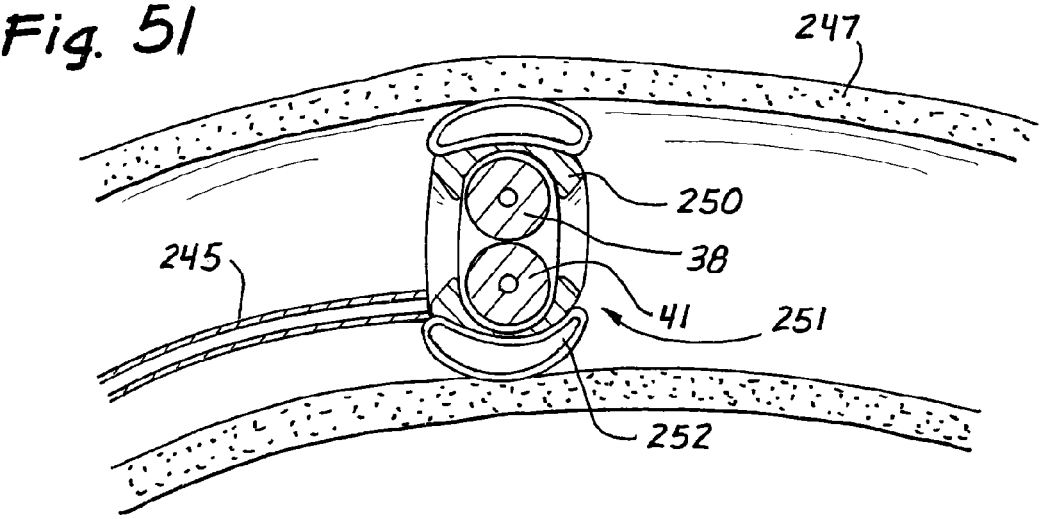
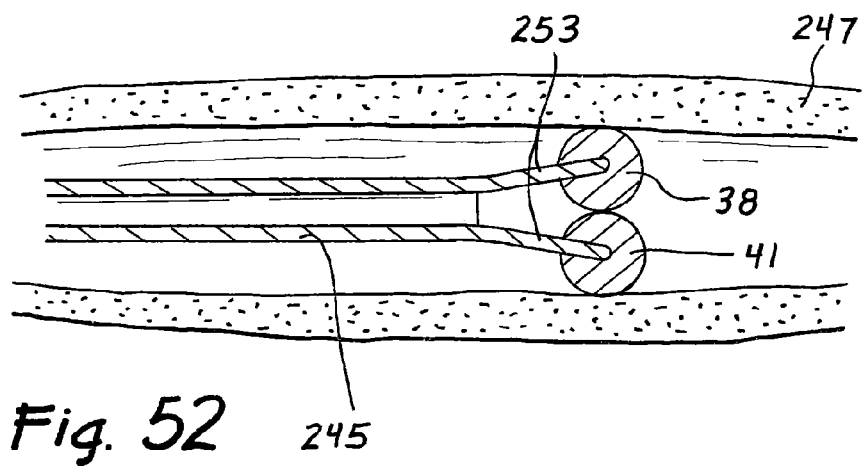
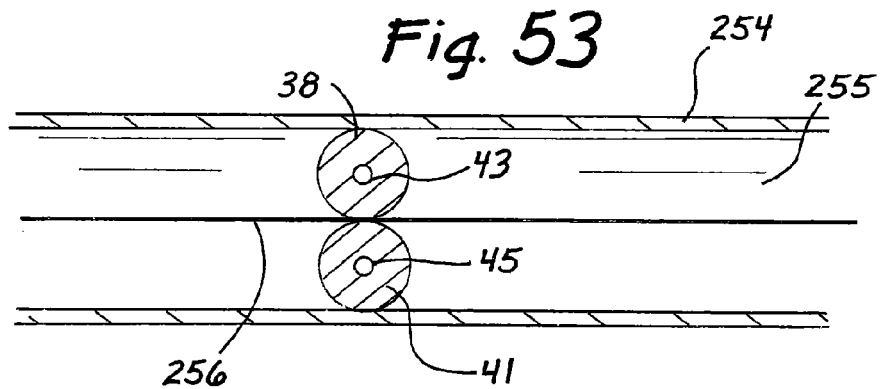

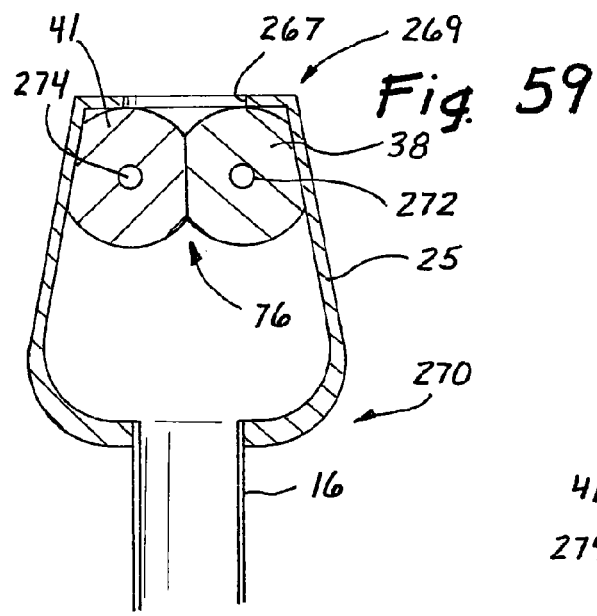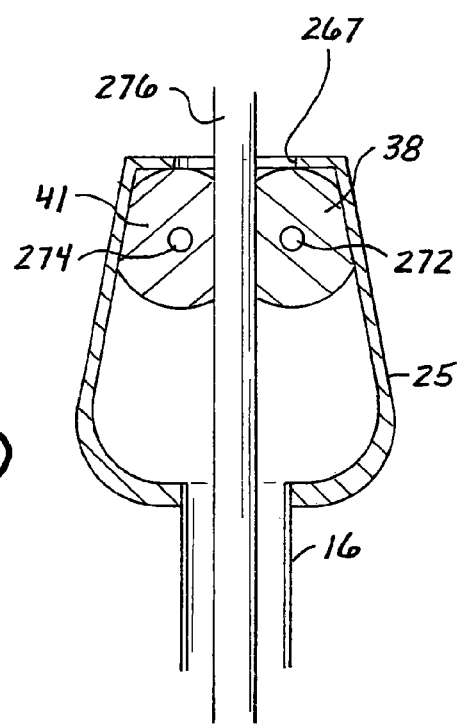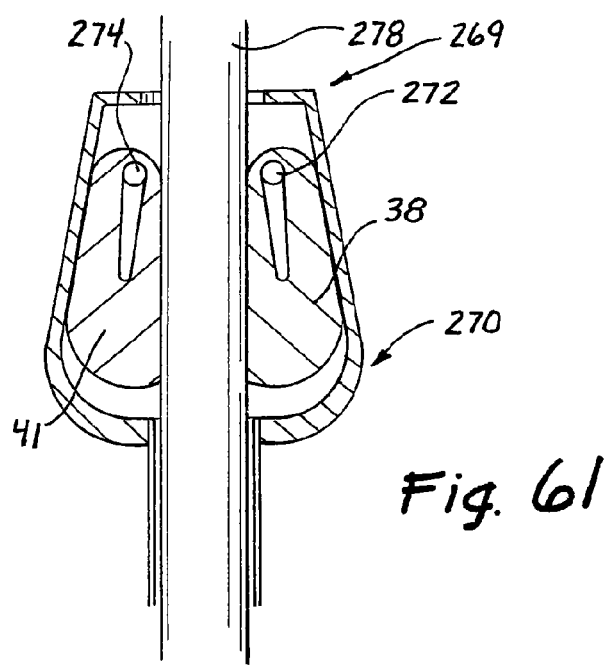
Fig. 59
Fig. 60
Fig. 61

ACCESS SEALING APPARATUS AND METHOD

CROSS REFERENCE TO RELATED APPLICATIONS

This application is a continuation of U.S. patent application Ser. No. 13/417,950, filed on Mar. 12, 2012, now U.S. Pat. No. 8,870,904, which is a continuation of U.S. patent application Ser. No. 12/791,607, filed on Jun. 1, 2010, now U.S. Pat. No. 8,157,835, which is a continuation of U.S. patent application Ser. No. 10/776,387, filed on Feb. 10, 2004, now U.S. Pat. No. 7,727,255, which is a continuation of International Application No. PCT/US2002/015696 filed on May 14, 2002, which published in English as International Patent Publication No. WO 2003/015848 A1 on Feb. 27, 2003, which claims the benefit of U.S. Application No. 60/312,683, filed on Aug. 14, 2001, of which the entire disclosures are incorporated herein by reference.

BACKGROUND OF THE INVENTION

Field of the Invention

This invention relates generally to access sealing devices and more specifically to surgical devices and methods providing a working channel for the insertion of instrumentation across a body wall and into a body cavity.

Discussion of the Relevant Art

Access devices in general are disposed relative to a conduit and are adapted to provide input to a flow of fluid through the conduit. The device will typically include a valve assembly which controls passage of the fluid in either a liquid state or a gas state. Such access devices might be adapted for use with fluids such as foods, oils, and grease, for example.

Devices of particular interest include surgical access devices which are commonly used to form a passage way across a body wall and into a body conduit or other body cavity.

This passageway enables a surgeon operating exteriorly of the body to perform surgical operations within the body cavity by manipulating instruments through the passageway. These instruments might include scopes, needles, graspers, clamps, staplers, sutures, and cutters, for example.

Of course the passageway, more commonly referred to as a working channel, also provides a path for fluids to exit the body from the body cavity. In order to inhibit this leakage of fluids, some access devices are provided with valves which can seal the working channel both in the absence of an instrument and in the presence of an instrument.

The sealing of the working channel is of particular importance in the case of laparoscopic surgeries where the abdominal cavity is inflated with an insufflation gas in order to distend the abdominal wall and thereby increase the size of the working environment. Trocars are commonly used as access devices for this type of surgery. The trocars include a cannula and a seal housing containing one or more valves which facilitate instrument access while inhibiting leakage of the insufflation gas.

In the past, trocar valves have typically included at least one zero valve intended to form a zero seal in the absence of an instrument, and at least one instrument valve intended to form an instrument seal in the presence of an instrument. Zero seals have typically been formed by duckbill seals which are incapable of also functioning as an instrument seal. The instrument seals have typically been formed by septum valves, having a hole or opening which is radially stretchable to some limited extent. With the limited stretchability of the septum valves, the trocars of the past have been able to accommodate only a small range of instrument diameters.

Due to this limited accommodation of instrument sizes, different trocars have been required in order to accommodate a full range of instrument sizes from almost zero mm to 12 mm. In some cases a smaller trocar would be used initially only to find that a larger instrument was required. In these instances, the smaller trocar had to be completely removed in order to inset a larger trocar to accommodate the larger instrument. As a result, a whole set of trocars, each having a different septum valve were required. Eventually, single trocars were provided having multiple septum valves of different sizes, along with a zero valve for each of the septum valves. Of course these instruments were much more complex and expensive.

In the past, septum valves were positioned along the axis of the working channel. However, it was observed that instrument seals would tend to leak if the instrument was moved off-axis. Accordingly, septum valves were provided with floating characteristics whereby the seal interface could be maintained even if the instrument was positioned off-axis. Of course, this floating of the septum seal required special structure which increased the cost of manufacture.

Septum valves have also been highly susceptible to tearing, particularly by instruments having sharp points. Elaborate guiding and protection mechanisms were provided to protect the septum seals against this type of instrument. Again, the sophisticated protection structures significantly increased the complexity of the device and the resulting cost of manufacture.

SUMMARY OF THE INVENTION

These deficiencies of the past are overcome with the present invention which includes a seal material in the form of a gel. The gel is highly compliant and stretchable. As a result of these properties, a single valve can function not only as a zero seal, but also as an instrument seal capable of accommodating the full range of instrument sizes. The increased compliance and stretchability of the gel material easily accommodates instruments which are moved off-axis, so no additional floating structure is required.

In a preferred embodiment, the valve is provided in the form of a roller having an axle supported by the seal housing. The valve can be rotatable on an axle having a fixed relationship with the seal housing or the valve can be rotatable with the axle relative to the seal housing.

In one aspect of the invention, a trocar is adapted to provide access for a surgical instrument through a body wall and into a body cavity. The trocar includes a cannula having a proximal end and a distal end, and a seal housing disposed at the proximal end of the cannula and defining with the cannula a working channel. A seal assembly is disposed within the housing and includes at least one roller, having an axis supported by the seal housing. The roller has properties for forming a zero seal in the absence of the instrument, and an instrument seal in the presence of the instrument.

In another aspect of the invention, a surgical combination includes an instrument having a diameter of at least five millimeters, and an access device adapted to facilitate disposition of the instrument across the body wall. A cannula is included in the access device along with a seal housing which forms a working channel with the cannula. A seal assembly is disposed in the housing and includes a roller sized and configured to form a zero seal in the absence of the instrument and an instrument seal in the presence of the instrument.

In an additional aspect of the invention, a trocar assembly includes a cannula having a proximal end and a distal end, a seal housing is disposed at the proximal end of the cannula and forms a working channel with the cannula. A roller is disposed in the seal housing and is pivotal on an axis. A resilient material included in the roller has properties susceptible to tearing in response to an instrument inserted into the working channel. The roller is moveable by the inserted instrument to pivot the resilient material relative to the axis and thereby inhibit tearing of the resilient material.

In a further aspect of the invention, the trocar assembly includes a roller having an outer surface pivotal on an axis and disposed in proximity to an inner surface of the seal housing. At least one wiper is disposed between the outer surface of the roller and the inner surface of the housing.

In an additional aspect of the invention, the trocar assembly includes a roller having an axle supported by the seal housing. The roller has properties for forming an instrument seal when the instrument is inserted into the working channel. A resilient material defines an outer surface of the roller, and portions of one of the resilient material and the axle define at least one void.

In another aspect of the invention, the trocar assembly includes a roller having a resilient outer surface and an axle for pivoting the outer surface relative to the inner surface of the seal housing. Portions of the inner surface of the seal housing define at least one recess configured and arranged to receive the axle.

The trocar assembly in a further aspect of the invention includes a valve disposed in the valve housing and formed of a compliant material. The valve has properties for forming a zero seal across the working channel in the absence of the instrument and an instrument seal across the working channel in the presence of the instrument. The instrument seal has a diameter in radial cross-section ranging from a lower limit of about zero millimeters to an upper limit in a range between about six millimeters and about 12 millimeters.

In still a further aspect of the invention, a trocar assembly includes a valve disclosed in the valve housing. The valve is moveable within the valve housing between a first position wherein the valve has first compression characteristics relative to the instrument, and a second position wherein the valve has second compression characteristics relative to the instrument. The housing includes a pair of opposing walls which diverge between the first position and the second position. The housing in axial cross-section has a triangular or trapezoidal configuration.

These and other features and advantages of the invention will become more apparent with a discussion of preferred embodiments in reference to the associated drawings.

DESCRIPTION OF THE DRAWINGS

FIG. 4A is a radial cross-section view taken along lines IVA-IVA of FIG. 3;

FIG. 4B is an axial cross section view taken along lines IVB-IVB of FIG. 4A;

FIG. 5 is a cross-section view similar to FIG. 3 and illustrating a pair of low-friction washers in another embodiment of the invention;

FIG. 6 is a perspective view of a gel roller adapted for use in the trocar of FIG. 1;

FIG. 7 is an axial cross-section view taken along lines VII-VII of FIG. 6;

FIG. 8 is an axial cross-section view similar to FIG. 3 with the rollers removed to show axle recesses;

FIG. 9 is an axial cross-section view similar to FIG. 8 and showing axle recesses with an oblong, vertical orientation;

FIG. 16 is an axial cross-section view similar to FIG. 7 and illustrating a roller with an axis and an axle having a spring configuration;

FIG. 17 is an axial cross-section view similar to FIG. 16 and illustrating an axle with an irregular outer surface forming a concave annulus;

FIG. 18 is an axial cross-section view similar to FIG. 17 wherein the irregular surface on the axle comprises at least one convex annulus;

FIG. 19 is a cross-section view similar to FIG. 17 wherein the irregular surface is formed by rotating at least one straight line about the axis;

FIG. 32 is an axial cross-section view similar to FIG. 31 wherein the housing wiper elements define the working channel both proximally and distally of the rollers.

FIG. 33 an axial cross-section view similar to FIG. 3 with four rollers forming multiple reservoirs;

FIG. 34-35 illustrate an embodiment wherein the rollers are positioned radially and are pivotal on a floating ring axle;

FIG. 34 is an axial cross-section view similar to FIG. 3 and showing two of the radially positioned rollers;

FIG. 35 is a radial cross-section view of the radially spaced roller seals taken along lines XXXV-XXXV of FIG. 34;

FIG. 36 is an axial cross-section view showing the roller with a toroidal configuration;

FIG. 37 is a cross-section view of the toroidal roller taken along lines XXXVII-XXXVII of FIG. 36;

FIG. 38 is an axial cross-section view of an additional embodiment including idler rollers;

FIG. 39 is an axial cross-section view similar to FIG. 3 wherein the axles of the rollers are pivotal relative to the housing;

FIG. 44 is an axial cross-section view similar to FIG. 31 with a single roller pivotal relative on the housing;

FIG. 45 is an axial cross-section view similar to FIG. 44 and including two opposing rollers pivotal on the housing;

FIG. 46 is an axial cross-section view similar to FIG. 3 including pivoting levers which extend from the seal housing to engage the roller;

FIG. 47 is an axial cross-section view similar to FIG. 3 wherein the working channel through the seal housing is lined with a tubular braid;

FIG. 48 is an axial cross-section view similar to FIG. 3 wherein the rollers are covered with braid or fabric sleeves;

FIGS. 49-50 illustrate a roller valve in a seal housing adapted for use to facilitate fluid flow from an inlet to an outlet of the housing;

FIG. 49 is an axial cross-section view showing the rollers engaging each other in the seal housing in response to fluid back pressure;

FIG. 50 is an axial cross-section view similar to FIG. 49 showing deformation of the seals to create a fluid passageway in response to fluid forward pressure;

FIG. 51 is an axial cross-section view of a further embodiment wherein rollers are combined with a circumferential balloon element to form a catheter adapted for use within a body conduit;

FIG. 52 is an axial cross-section view of a catheter having rollers at its distal end;

FIG. 53 is an axial cross-section view of an embodiment including a shaft and a pair of rollers moveable within the shaft to form an instrument seal with a suture;

FIGS. 54-55 illustrate an embodiment similar to that of FIG. 35 wherein the rollers are disposed in an associated quadrant of the seal housing;

FIG. 54 is an axial cross-section view similar to FIG. 34;

FIG. 55 is a cross-section view of the rollers seals taken along lines LV-LV of FIG. 54;

FIG. 59 is a top plan view of the seal housing in FIG. 56;

FIG. 60 is a top plan view of the seal housing in FIG. 57;

FIG. 61 is a top plan view of the seal housing in FIG. 58; and

DESCRIPTION OF PREFERRED EMBODIMENTS AND BEST MODE OF THE INVENTION

Figure 1:
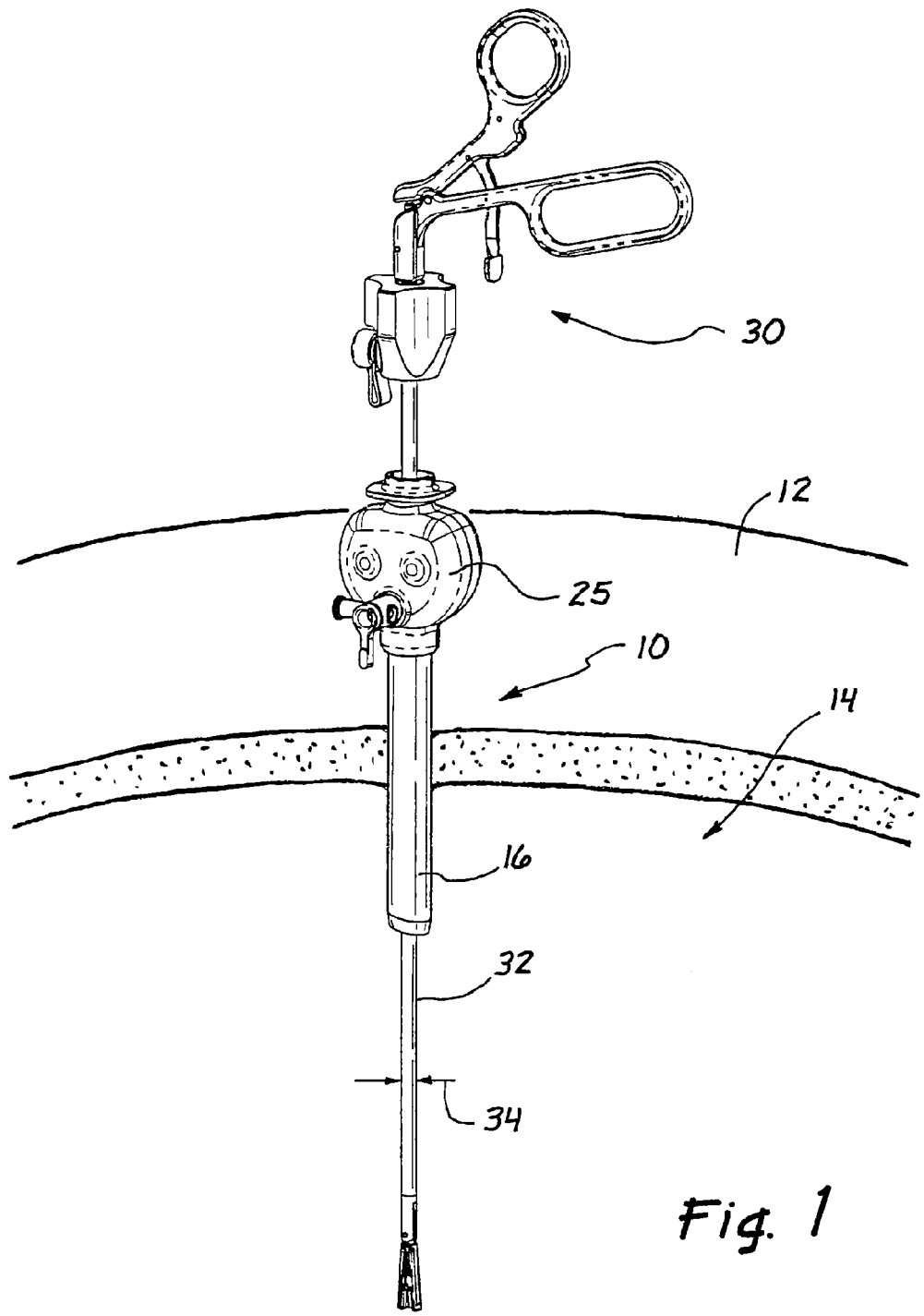
FIG. 1 is a perspective view showing a laparoscopic surgery with a surgical instrument in the form of a grasper inserted through a working channel of a trocar of the present invention.
Figure 2:
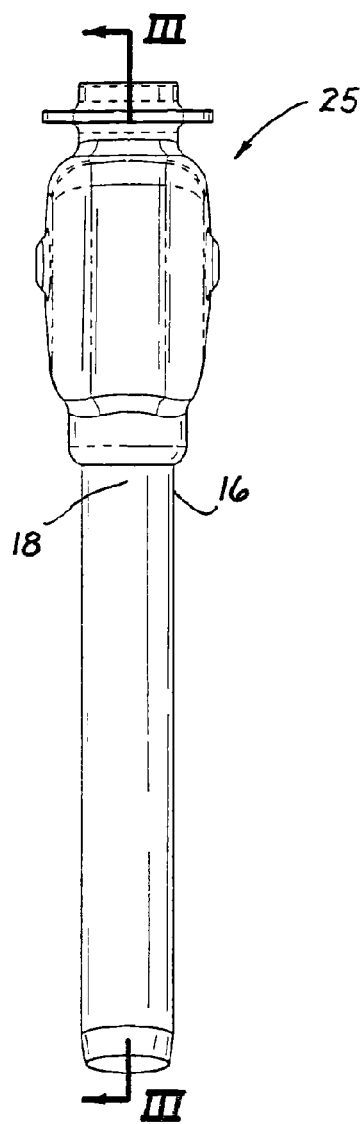
FIG. 2 is a side elevation view of the trocar illustrated in FIG. 1.

A trocar is illustrated in FIG. 1 and designated by the reference numeral 10. The trocar 10 is operatively disposed to provide access across a body wall, such as the abdominal wall 12, and into a body conduit or cavity, such as the abdominal cavity 14. In this case, the trocar 10 is representative of any access device which extends across a body wall to provide access into a body conduit or cavity. The access device may facilitate a flow of fluids, either gas or liquid, into or out of the conduit or cavity 14. Alternatively, the access device may accommodate a surgical instrument, such as a needle, which can be inserted through the access device and into the body conduit or cavity 14.

In the illustrated embodiment, the trocar 10 includes a cannula 16 which extends along an axis 18 between a proximal end 21 and a distal end 23. A seal housing 25 is disposed at one of the proximal end 21 and the distal end 23 of the cannula 16, and forms with the cannula 16, an access or working channel 27. This working channel is sized and configured to receive a surgical instrument 30, such as a grasper, which will typically include an elongate tube or shaft 32 having a maximum dimension or diameter, shown by arrows 34.

In this case, the grasper or instrument 30 is representative of any surgical instrument or device which might be inserted through the working channel 27 of the trocar 10 and into the body cavity, such as the abdominal cavity 14. Other instruments may be as small as a suture (not shown) which might have a diameter less than one millimeter, as well as scopes, cutters, clip appliers, clamps and even staplers, which might have a diameter as large as 12 millimeters.

In general, it may be desirable that the access device, such as the trocar 10, have properties for inhibiting the egress of fluids outwardly through the working channel 27. This is particularly important in the case of laparoscopic surgeries where the abdominal cavity 14 is typically inflated with a gas in order to elevate the abdominal wall 12 and thereby increase the volume of the working environment. The sealing of the working channel 27 is of course complicated by the desire to introduce instruments, such as the grasper, along the working channel 27. Not only is sealing of the working channel 27 desired in the absence of the instrument 30, but it is also desired when the instrument 30 is operatively disposed as illustrated in FIG. 1.

Figure 3:
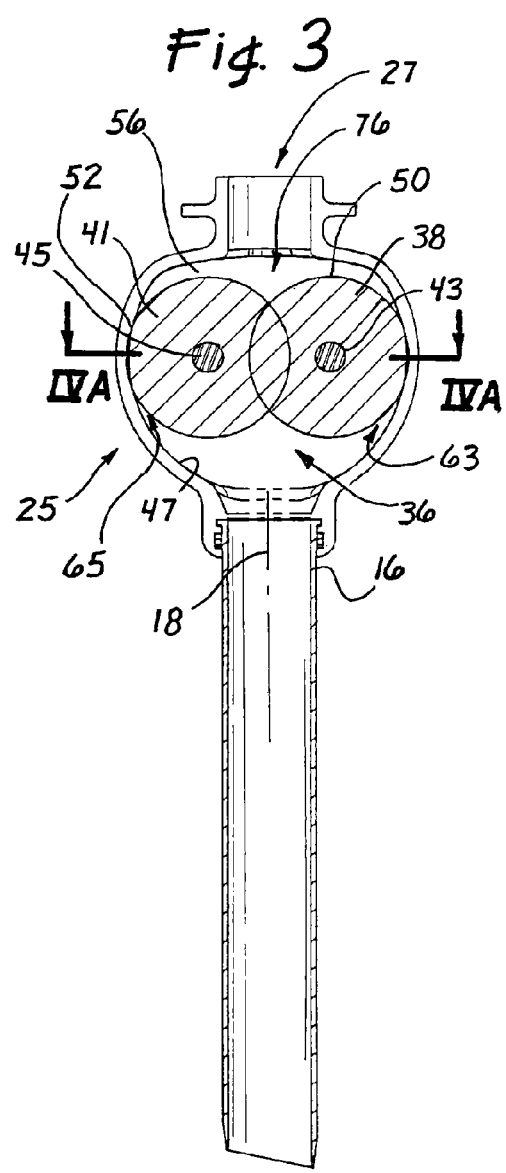
FIG. 3 is an axial cross-section view taken along lines III-III of FIG. 2.

A seal assembly 36 of the present invention is illustrated in the axial cross-section view of FIG. 3. This seal assembly includes two rollers 38 and 41, having axles 43 and 45, respectively. The rollers 38 and 41 are rotatable on respective axes and relative to an inner surface 47 of the seal housing 25. The axles 43 and 45 may be rotatable with the respective rollers 38 and 41 relative to the housing 25, or may be fixed to the seal housing 25 in which case the rollers 38 and 41 also rotate relative to their respective axles 43 and 45.

In the embodiment of FIG. 3, the rollers 38 and 41 each have a cylindrical outer surface as well as a pair of end surfaces. For example, the roller 38 has a cylindrical outer surface 50 best illustrated in FIG. 3, as well as a pair of end surfaces 52 and 54, best illustrated in FIG. 4A. The roller 41 is similarly constructed with a cylindrical outer surface 56 and a pair of end surfaces 58 and 61.

In order to form the desired seals across the working channel 27, it is important that the rollers 38 and 41 form each lateral seals and end seals with the inner surface 47 of housing 25. Thus, in a preferred embodiment, lateral seals 63 and 65 are formed between the seal housing 25 and the respective cylindrical surfaces 50 and 56. Similarly, end seals are formed between the seal housing 25 and the end surfaces of each of the rollers 38 and 41. For example, end seal 67 and 70 are formed between the seal housing 25 and the end surfaces 52 and 54 of the roller 38. Similar end seals 72 and 74 are formed between the seal housing 25 and the end surfaces 58 and 61 of the roller 41. In combination, the lateral seals 63, 65 and the end seals 67-74 form a continuous seal between the seal assembly 36 and the seal housing 25. Importantly, the rollers 38 and 41 also form a zero seal 76 or an instrument seal 78 which are necessary to close the working channel 27 both in the absence of the instrument 30 and in the presence of the instrument 30, respectively.

In the illustrated embodiment, the zero seal 76 is formed between the rollers 38 and 41 in the absence of the instrument 30. Collectively, the lateral seals 63, 65, the end seal 67-74, and the zero seal 76 close off or seal the working channel 27 in the absence of the instrument 30.

When the instrument 30, such as the grasper, is inserted into the trocar 10, as illustrated in FIG. 1, the instrument seal 78 is formed between the shaft 32 and the rollers 38, 41. Collectively, the lateral seal 63-65, the end seals 67-74, and the instrument seal 78 close off or seal the working channel 27 in the presence of the instrument 30.

Given the desire to form the various seals including the lateral seals, the end seals, the zero seal, and the instrument seal, it can be appreciated that a special material is required for the rollers 38 and 41. A material of particular interest is that disclosed by applicant in U.S. Patent Application Ser. No. 60/241,958 filed on Oct. 19, 2000, entitled "Hand-Assisted Laparoscopy Apparatus and Method," which is incorporated herein by reference. This particular material is a gel material 80 which has properties including a low durometer hardness and a high tear strength. In addition, the gel material 80 tends to have float characteristics similar to a fluid in that it is easily displaced, for example, by insertion of an instrument, without affecting the instrument seal. Although the gel has characteristics of a fluid, it also has characteristics of a solid in that it can be formed, for example, molded to a desired shape.

Various coatings or lubricants can be applied to the sealing surfaces of the rollers 38 and 41 to facilitate formation of the various seals.

Given these characteristics, the gel material of the rollers 38 and 41 can easily form the zero seal 76, and upon insertion of the instrument 30, easily form the instrument seal 78. Importantly, the instrument seal 78 can accommodate a wide range of instrument diameters. For example, a suture having a diameter of only about one millimeter can be easily accommodated by the rollers 38 and 41. And when a large instrument having a diameter such as 12-15 millimeters, is inserted, the instrument seal 76 can compliantly expand to accommodate the larger diameter. As a result, the single trocar 10, having but a single valve formed by the rollers 38 and 41, can accomplish all of the sealing desired whether in the absence of the instrument 30 or in the presence of the instrument 30, and regardless of instrument diameters.

These advantages can accrue to any embodiment merely having a gel disposed within the seal housing 25. In the illustrated embodiment, it is the gel material 80 and its float characteristics which form the highly complaint instrument seal capable of accommodating a wide range of diameters. Forming this gel material 80 into a roller, such as the rollers 38 and 41, adds the further advantage of protecting the gel material against any tendency to tear or propagate due to insertion of a sharp instrument. With the roller configuration, a sharp point engaging the outer surface of the roller 38, for example, will cause the roller 38 or 41 to rotate on its axis and ultimately disengage the sharp instrument point without tearing the gel material 80. A further advantage of having two of the rollers 38, 41, is that the instrument 30 tends to be centered along the axis 18 within the working channel 27. Also, with two cylindrical rollers, more than one instrument may be inserted at the same time, in which case two of the instrument seals 78 are formed. For example, if a grasper is used to insert a suture, instrument seals 78 are formed around each of the grasper and the suture.

Providing the rollers 38 and 41 with an ability to move or rotate relative to their axes, facilitates the introduction of an instrument by changing a frictional resistance to a rolling resistance at the instrument seal 78. Of course, as the rollers 38 and 41 rotate, frictional resistance is encountered at the lateral seals 63 and 65 as well as the end seals 67-74. This frictional resistance can be reduced by providing the inner surface 47 of the housing 25 with a low friction coating. Alternatively, pockets of lubricating material, discussed in greater detail below, can be formed to reduce the friction associated with these seals. Friction at the end seals 67-74 can also be addressed by providing low-friction washers, such as those designated by the reference numerals 81 and 83 in FIG. 5. These washers can be centered on the axles 43 and 45 of the rollers 38 and 41, respectively, so that the end seals 67-74 can be maintained with a reduced friction on the rollers 38 and 41. The washers 81 and 83 can be made of a polytetrafluoroethylene material or alternatively can be formed of a fabric material.

The individual rollers 38 and 41 and their associated axles 43 and 45, respectively, can be formed as illustrated in FIGS. 6 and 7. For example, the axles 43 and 45 can be formed of a rigid plastic with the gel material 80 molded to the axle 43. The cylindrical outer surface 56, as well as the end surfaces 61 and 63, of the roller 38 are also illustrated in FIGS. 6 and 7.

In the illustration of FIG. 8, the rollers 38 and 41 are not shown in order to illustrate axle recesses 85 and 87 which can be formed on each of the end walls associated with the housing 25. These recesses 85 and 87 can be sized and configured to rotatably receive the axles 43 and 45. The recesses 85, 87 most easily accommodate an embodiment wherein the gel material 80 and the associated axle, such as the axle 43, have a fixed relationship. In such an embodiment, the axle 43 is supported within the recess 85, and the entire roller, including the axle 43 and gel material 80, rotates relative to the housing 25.

In the embodiment of FIG. 9, the recesses 85 and 87 are formed with an oblong configuration in radial cross section. The recess 85, for example, has a length and a width and the length is oriented generally parallel to the axis 18. In such an embodiment, the axle 43 of the roller 38 would be disposed in the recess 85. With its elongate configuration, the recess 85 would accommodate both rotation and translation of the roller 38. Thus, the axle 43 might be biased toward the proximal end of the recess 85 but permitted to rotate and translate distally with insertion of an instrument. The translation offered by this embodiment would tend to reduce the insertion forces on the instrument 30.

Figure 10:
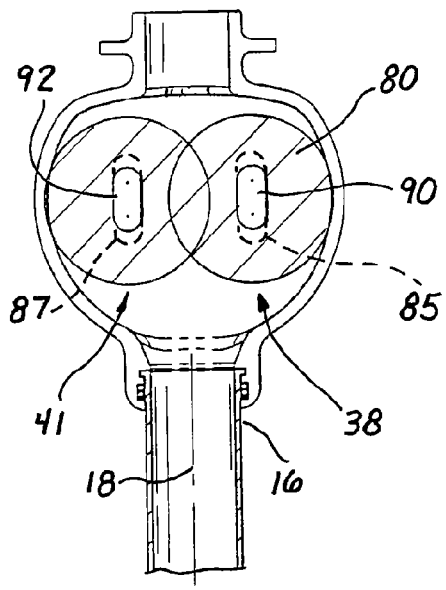
FIG. 10 is an axial cross-section view similar to FIG. 8 and illustrating a pair of rollers each with axles oblong in cross-section.

The oblong recesses 85 and 87 could also accommodate axles 90 and 92 that are oblong and cross section as illustrated in FIG. 10. With the length of the oblong cross section oriented generally parallel to the axis 18, greater axial support is provided for the roller 38. This orientation also reduces the transverse axle 90 in order to accommodate larger instruments between the two axles 90 and 92. The oblong axles 90 and 92 would typically have a fixed relationship with the housing 21, so the gel material 80 would rotate about the axle 90 and 92 in this embodiment. Translation could be provided by recesses 85 and 87 having a greater length than that of the axle cross-section.

Figure 11:
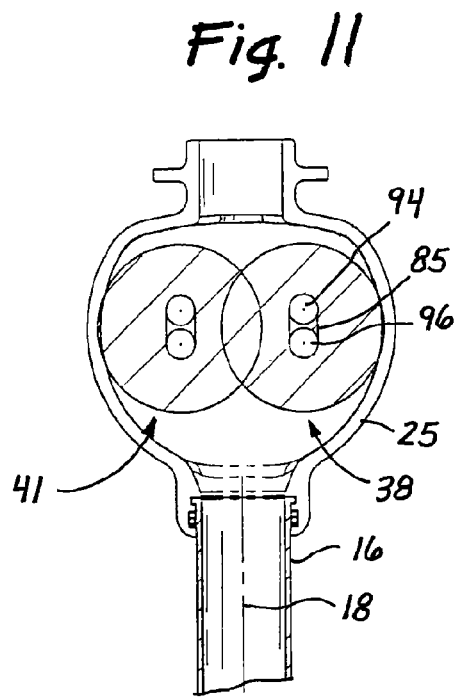
FIG. 11 is an axial cross-section view similar to FIG. 8 and illustrating rollers with a pair of axially oriented in-line axles.
Figure 12:
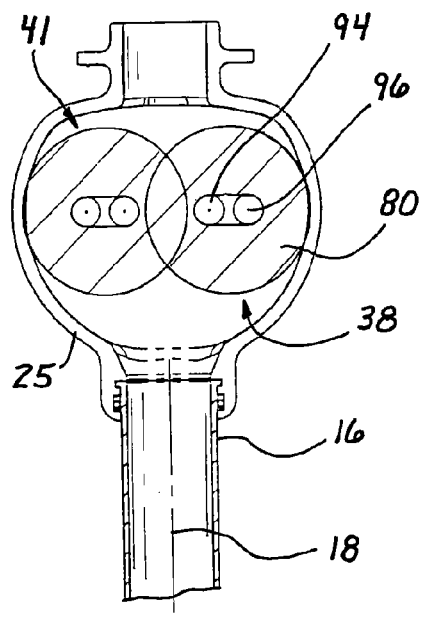
FIG. 12 is an axial cross-section view similar to FIG. 8 and showing in-line axles with a radial orientation.

In a further embodiment of the invention illustrated in FIG. 11, the rollers 38 and 41 are each formed with a pair of in-line axles. For example, the roller 38 includes cylindrical axles 94 and 96 which may be rotatable within a common oblong recess, such the recess 85. The axles 94 and 96 in the illustrated embodiment are aligned longitudinally or generally parallel to the axis 18. The gel material 80 in this particular embodiment is rotatable relative to the axles 94 and 96 which are in turn rotatable with respect to the seal housing 25. With this configuration, the in-line axles 94, 96 function as needle bearings rotatably supporting the gel material 80 which functions as a conveyor belt. This construction tends to further reduce insertion forces encountered by the instrument 30. Of course the in-line axles 94 and 96 could be oriented laterally of each other as illustrated in FIG. 12, or generally disposed, at any other angle relative to the axis 18.

Figure 13A:
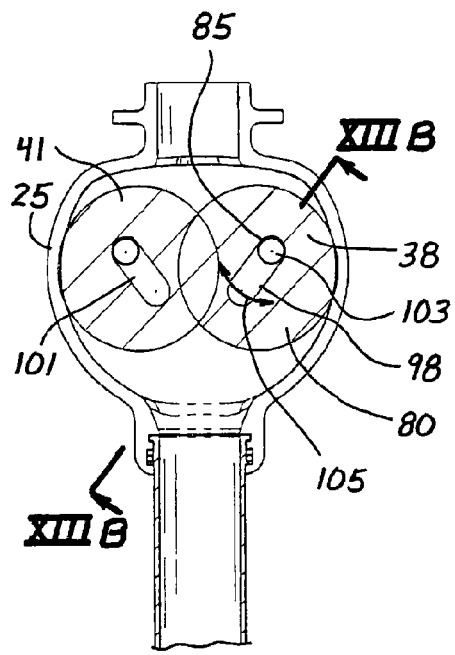
FIG. 13A is an axial cross-section view similar to FIG. 8 and illustrating rollers with oblong axles pivotal with respect to the working channel of the trocar.
Figure 13B:
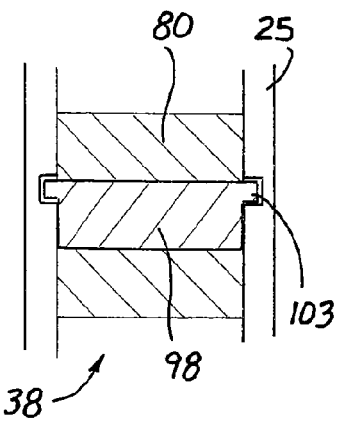
FIG. 13B is a cross-section view taken along lines XIIIB-XIIIB of FIG. 13A.

In the embodiment of FIG. 13A, the rollers 38 and 41 are mounted on axles 98 and 101, respectively, having an oblong configuration. In this case, the axle 98, for example, is provided with a cylindrical mounting pin 103 which is sized and configured to be received in the associated recess 85. With the pin 103 disposed at one end of the oblong cross-section, as shown in FIG. 13B, the roller 38 will tend to pivot, perhaps against a spring bias, as the instrument is inserted. In this case, translation of the roller 30 is along an arc shown generally by the arrow 105 in FIG. 13A.

Figure 14:
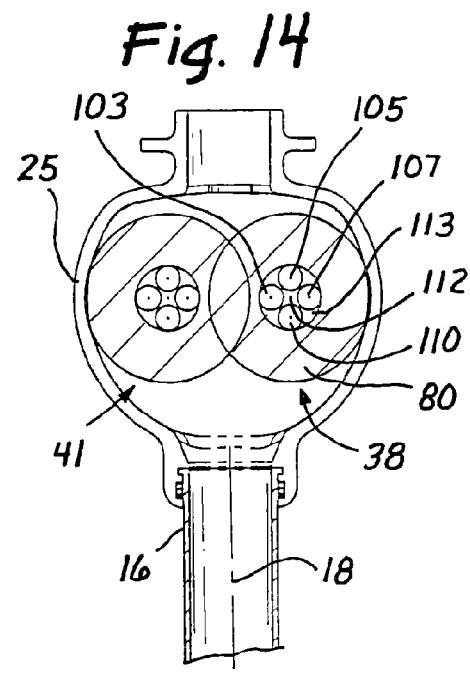
FIG. 14 is an axial cross-section view similar to FIG. 8 and illustrating rollers with radially-spaced axles.

The structure of FIG. 14 is similar to that of FIG. 11 in that the rollers 38 and 41 are provided with multiple axles. In this embodiment, for example, the roller 38 has four axles, 103, 105, 107 and 110 which are rotatable on individual axes, and also revolve about a common line shown as a point 112 in FIG. 14. With the gel material 80 of the roller 38 provided with a cylindrical inner hole 113, its rotation, is greatly facilitated by the multiple axles 103-110 which function as needle bearings.

Figure 15A:
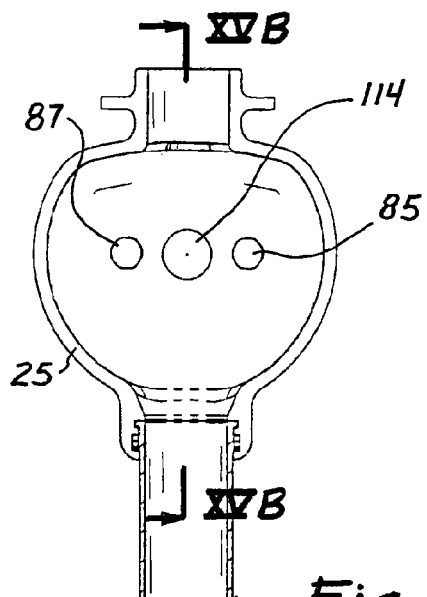
FIG. 15A is an axial cross-section view similar to FIG. 8 and illustrating a convex protrusion disposed between axle recesses.
Figure 15B:
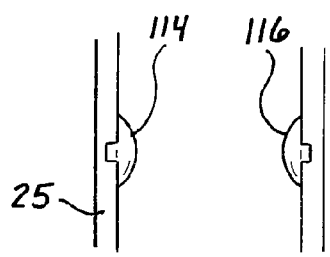
FIG. 15B is a cross-section view taken along lines XVB-XVB of FIG. 15A.

The embodiment of FIG. 15A is similar to that of those previously discussed except that this embodiment includes a protrusion 114 which extends inwardly of the seal housing 25. In the illustrated embodiment, the protrusion 114 is disposed between the recesses 85 and 87 and has a convex configuration. With an opposing protrusion 116 extending inwardly from the opposite wall as shown in FIG. 15B, the protrusions 114 and 116 function to center the instrument 30 along the rollers 38 and 41, which for clarity are not shown in this view. The convex protrusions 114 and 116 also serve to add additional compression on the end surfaces of the rollers in order to aid in sealing around the inserted instrument 30.

A preferred embodiment of the roller 38 was described with references to FIGS. 6 and 7. Many other embodiments of the roller 38 will now be apparent to those of ordinary skill in the art. These additional roller embodiments will typically be formed with a fixed relationship between the axle 43 and the gel material 80. Nevertheless, as previously noted, the roller 38 can be formed with the axle 43 maintained in a fixed relationship with the seal housing 25. In this latter case, the gel material 80 would typically revolve about the fixed axle 43.

One of the additional roller embodiments is illustrated in FIG. 16 where the axle 43 is formed as a spring. With this configuration, the axle is slightly bendable or deformable along its length, thereby aiding in the ability of the roller 38 to conform to the shape of inserted instrument 30 such as the grasper.

Another roller embodiment is illustrated in FIG. 17 wherein the axle 43 has a shape other than the cylindrical shape illustrated in the embodiment of FIG. 7. In this case, the axle 43 has an angular groove 118 which is disposed within the gel material 80. This groove 118 facilitates orientation of the gel material 80 relative to the axle 43. Particularly in an embodiment wherein the gel material 80 revolves around a fixed axle 43, the groove 118 facilitates a preferred disposition of the gel material 80 centered on the axle 43.

With reference to FIG. 18, it can be appreciated that the centered relationship between the gel material 80 and the axle 43 can actually be facilitated by angular protrusions designated by the reference numeral 121. These protrusions 121 can be formed as a surface of revolution defined by multiple semi-circles as illustrated in FIG. 18. Alternatively, the protrusions 121 might be formed as surfaces of revolution defined by straight lines, perhaps forming peaks and valleys as illustrated in the embodiment of FIG. 19.

Figure 20:
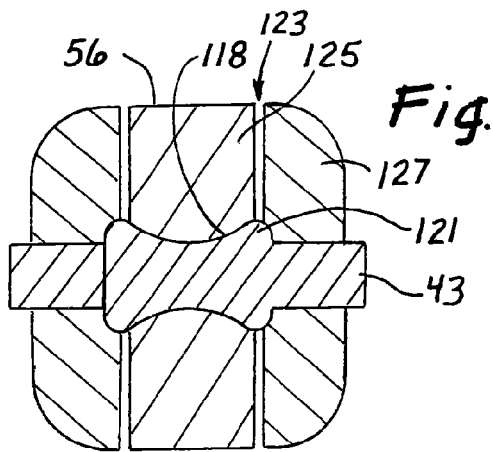
FIG. 20 is an axial cross-section view similar to FIG. 17, wherein the irregular surface of the axle is formed with both concave and convex surfaces, and the gel roller is formed with a circumferential slit which extend radially to the axle.

In the embodiment of FIG. 20, the axle 43 is similar to that of FIG. 17 in that it includes an angular groove 118. It is also similar to the embodiment of FIG. 18 in that it includes protrusions 121. In each of the embodiments disclosed in FIG. 17-20, the non-cylindrical shape of the axle 43 serves to circumferentially compress the gel material 80 around any inserted instrument 30 to facilitate sealing and minimize any tendency toward a "cat-eye" effect In the embodiment of FIG. 20 the gel material 80 is formed with at least one groove 123 which begins at the cylindrical surface 56 and extends inwardly toward the axle 43. It is the purpose of the groove 123 to facilitate compliance of the gel material 80 with the instrument 30. This enhances formation of the instrument seal 78 by dividing the gel material into discreet sections 125 and 127. Of course these sections can be defined by any groove extending inwardly from a surface of the gel material 80. The groove 123 need not be planar, but can have a curved or rounded configuration. It can also be disposed at any angle with respect to the axle 43, not just the 90-degree angle illustrated in FIG. 20.

Figure 21:
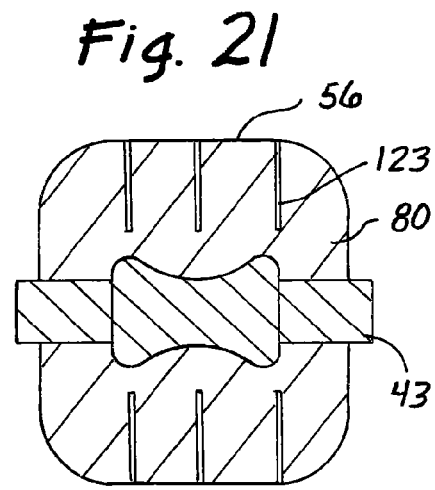
FIG. 21 is a cross-section view similar to FIG. 20 wherein the circumferential slits are terminated short of the axle.
Figure 22:
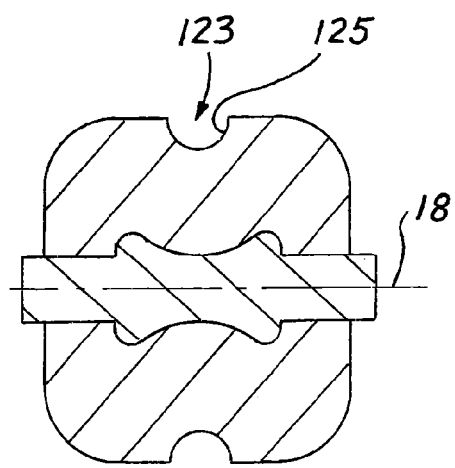
FIG. 22 is an axial cross-section view wherein the gel roller has a circumferential groove.

The groove 123 can have a constant width or even a variable width in different embodiments. The groove 123 can extend from the cylindrical surface 56 to the axle 43, as illustrated in FIG. 20, or can extend only a portion of this distance as illustrated in FIG. 21. It can also be formed as a surface of revolution about the axis 18. For example, in FIG. 22, this surface of revolution is defined by a semi-circle 125.

Figure 23:
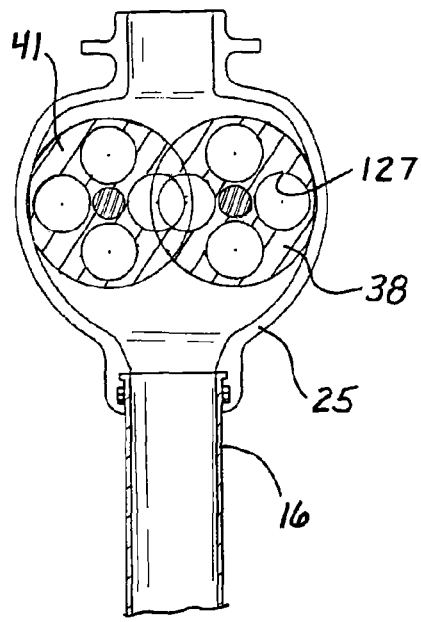
FIG. 23 is an axial cross-section view similar to FIG. 3 wherein the gel of the rollers is formed with multiple voids.

Grooves such as the groove 123, which facilitates compliance of the gel material 80 with the instrument 30, can also be formed interiorly of the gel material 80 as illustrated by the voids 127 in FIG. 23. These voids 127 also create space into which the gel material can more easily flow to provide the desired compliance characteristics. The voids 127 can take generally any shape, not just the cylindrical shape illustrated in the cross-sectional view of FIG. 23. The gel voids 127 can extend to a surface of the gel material 80 or be defined entirely within the gel material 80.

Figure 24:
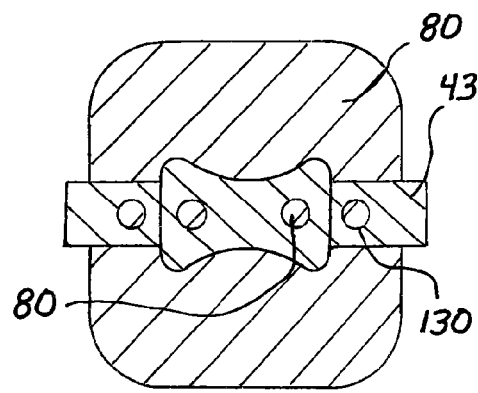
FIG. 24 is an axial cross-section view similar to FIG. 17 wherein the axle includes holes configured to receive a portion of the gel material forming the roller.

Voids can also be created in the axle 43, but for a entire different purpose. Such voids are illustrated in FIG. 24 and designated by the reference numeral 130. The purpose of these voids 130 is to facilitate a flow of the gel material into the voids 130 as the gel material 80 is insert molded onto the axle 43. With the gel 80 extending outwardly of the axle 43 and through the voids 130 of the axle 43, the fixed relationship between these two structures is greatly facilitated.

Figure 25:
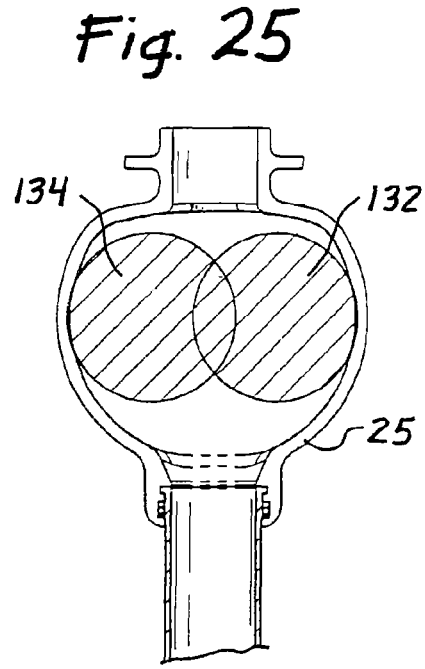
FIG. 25 is an axial cross-section view similar to FIG. 24 wherein the rollers are formed without axles.

In other embodiments, the gel material 80 can be formed into a plurality of independent structures 132 and 134 which may either have a fixed relationship or a moveable relationship with respect to the seal housing 25. In embodiments wherein the structures 132 and 134 are moveable, the absence of axles could facilitate movement of the structures 132 and 134 in an independent and random manner. Such movement might include both rotational movement, as well as translational movement. Although the gel structures 132 and 134 and FIG. 25 are illustrated to have a cylindrical configuration, it will be apparent that the number and shape of the various gel structures 132, 134 may vary considerably in different embodiments of the invention.

Figure 26:
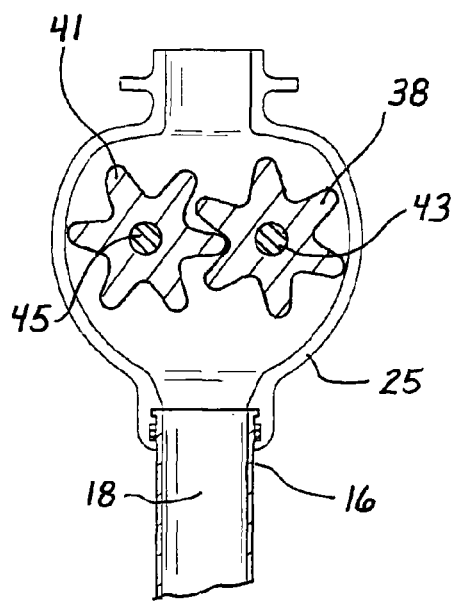
FIG. 26 is an axial cross-section view similar to FIG. 24 wherein the rollers in the radial cross-section have the shape of a star.

The outer surface of the gel material 80 can also have many different forms as illustrated by the embodiment of FIG. 26. In this cross-sectional view, the rollers 38 and 41 have an outer surface defined by alternating peaks and valleys. In the cross-section view, these rollers 38, 41 have the configuration of a star and are oriented with respect to each other so that the peaks of each roller 38, 41 align with the valleys of the opposing roller 41, 38 in a mesh-gear configuration.

Figure 27:
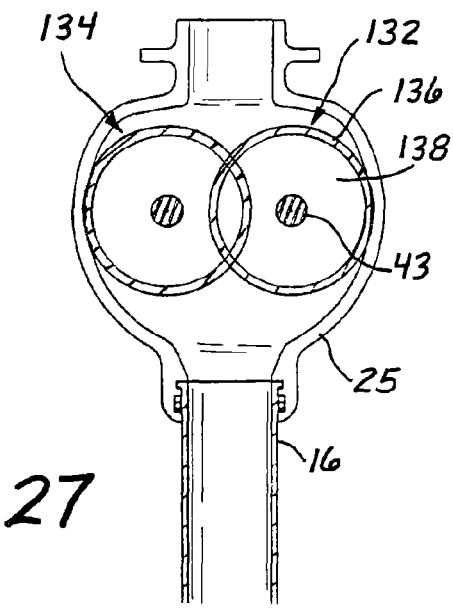
FIG. 27 is an axial cross-section view similar to FIG. 24 wherein the rollers are formed as inflated bladders.

FIG. 27 illustrates an embodiment wherein the rollers 38 and 41 are configured as inflatable bladders 132 and 134. The bladder 132 will typically be formed as a cylinder having an outer skin 136 supported at its ends on the axle 43. This skin 136 defines an interior cavity which can be inflated, typically with an inflating material 138 which may be fluid or semi-fluid such as a gas or liquid. Thus inflated, the bladder 132 is provided with characteristics which are highly compliant and therefore beneficial to the formation of the instrument seal 78. The skin 136 can be formed from a gel of the type previously disclosed or can be formed from a less compliant material. Particularly with the rolling characteristics, this embodiment will not be particularly susceptible to puncture.

Figure 28:
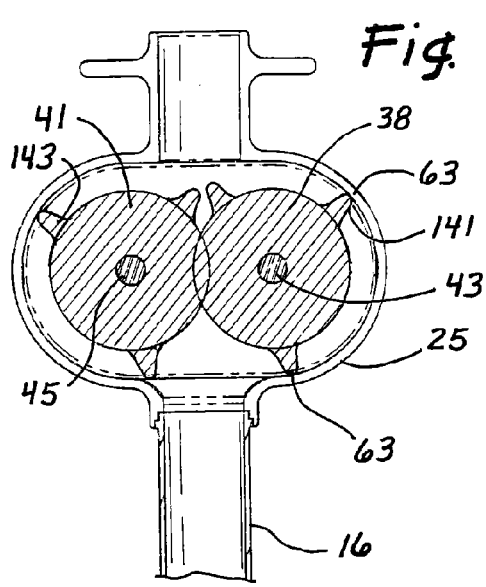
FIG. 28 is an axial cross-section view similar to FIG. 3 wherein the rollers are provided with wiper elements.

A further embodiment of the invention is illustrated in FIG. 28 wherein the rollers 38 and 41 are illustrated to include wiper seals 140 and 143, respectively. These wiper seals 140, 143 extend outwardly from the cylindrical surface 56 toward the inner surface of the seal housing 25. As the rollers 38 and 41 revolve about their respective axles 43 and 45, at least one of the wipers 141 and at least one of the wipers 143, respectively, form the lateral seals 63, 65 and end seals 67-74 with the housing 25. With a reduced area of contact between the wipers 141, 143 and the seal housing 125, there is a decrease in the frictional resistance associated with rotation of the rollers 38 and 41. Reduced frictional resistance is desirable as it decreases instrument insertion forces.

Figure 29:
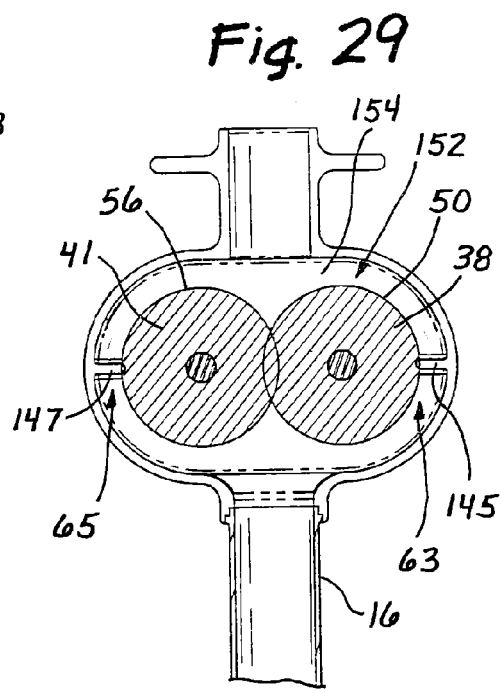
FIG. 29 is an axial cross-section view similar to FIG. 28 wherein the seal housing is provided with wiper elements.

In the embodiment of FIG. 29, this reduced frictional resistance associated with the lateral seal 63 and 65 is maintained with a structure wherein the seal housing 25 is formed with wipers 141 and 147 that extend inwardly to contact the cylindrical surfaces 50 and 56 of the rollers 38 and 41, respectively. With the wipers 141 and 147 having a stationary or fixed relationship with the housing 25, they also define with the rollers 38 and 41 a pocket 152 which can be filled with a fluid or semi-fluid material 154 such as a lubricant or antiseptic. This material is initially maintained in the pocket 152 but ultimately coats the rollers 138, 141 as they rotate in response to insertion of the instrument 30.

Figure 30:
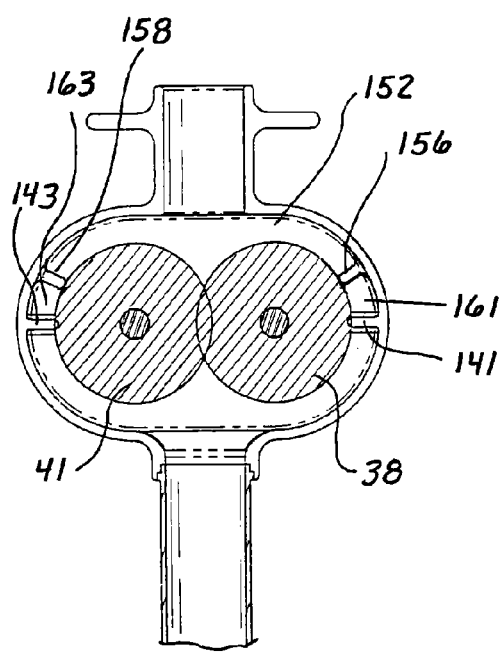
FIG. 30 is an axial cross-section view similar to FIG. 29 wherein the wiper elements of the housing form a reservoir.

Multiple pockets, such as the pocket 152 can be formed by providing additional wipers 156 and 158 as illustrated in FIG. 30. In this case, a pocket 161 is formed between the wipers 141 and 156, while a pocket 163 is formed between the wipers 143 and 158. Different materials can be disposed in the different pockets 161, 163.

Figure 31:
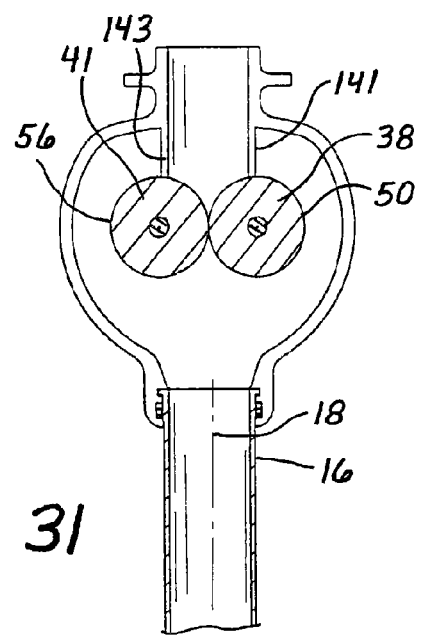
FIG. 31 is an axial cross-section view similar to FIG. 29 wherein the housing wiper elements define a portion of the working channel.

In the embodiments of FIGS. 29 and 30, the stationary wipers 141, 143 extend laterally, transverse to the axis 18. In the embodiment of FIG. 31, these wipers 141 and 143 extend axially from the seal housing 25 into contact with the cylindrical surfaces 50 and 56, respectively. With this configuration, the wipers 141, 143 also function as guides to facilitate introduction of the instrument 30 directly between the rollers 38 and 41.

With reference to the embodiment of FIG. 32, it will be appreciated that the stationary wipers 156 and 158 can also be oriented axially to facilitate formation of the pockets 161, 163 and to function further as guiding elements for the instrument 30.

Additional sealed pockets 165 and 170 can be formed in an embodiment including not only the rollers 38, 41, but two additional rollers 172 and 174. Such an embodiment is illustrated in FIG. 33.

The embodiment illustrated in FIG. 34 is most easily distinguished with reference to the cross-section of view of FIG. 35. In this embodiment, the gel material 80 is formed in multiple sections 181-186 which are positioned radially of the axis 18 and collectively form a toroid 190. The sections 181-186 are individually rotatable about a common axle 192 which also has a toroidal configuration. It will be noted that in this embodiment the zero seal 76, as well as the instrument seal 78, are formed interiorly of the toroidal axle 192. Maintaining the rotational characteristics of the individual sections 181-186 also facilitates insertion of the instrument 30 into the working channel 27.

With the gel material 80 in a toroidal configuration, it is particularly advantageous to form the seal housing 25 with a cross section that is circular as illustrated in FIG. 35. This circular cross section would be exhibited with the seal housing 25 having a conical or cylindrical configuration. The circular cross section is desirable since the toroidal gel material 80 is also circular on its outer edge. This facilitates formation of a single continuous seal between the housing 25 and the gel material 80. Thus, with the circular cross section, for the housing 25 and the toroidal configuration for the gel material 80, all seals necessary to seal the working channel both in the presence and in the absence of the instrument 30, are formed by the gel material 80. This configuration also greatly facilitates the manufacturing process where the toroidal gel material 80 is merely inserted into the conical or cylindrical seal housing 25.

These same characteristics are exhibited in a further embodiment, which is illustrated in FIG. 36 and the cross-sectional view of FIG. 37. In this case, the various sections 181-186 associated with the embodiment of FIG. 35 are formed in an integral configuration so that the toroid 190 rotates as a single unit around the toroidal axle 192. This embodiment is less expensive to manufacture but still maintains the advantages associated with the toroidal configuration.

FIG. 38 illustrates another embodiment which is similar to that of FIG. 29 except that the wipers 141 and 147 of that embodiment are replaced with idler rollers 194 and 196. These idler rollers 194, 196 can be supported on the seal housing 25 where they are permitted to rotate on their respective axes. The idler rollers 194 and 196 provide the lateral seals 63 and 65 between the seal housing 25 and the rollers 38 and 41, respectively. By including the idler rollers 194, 196, frictional resistance associated with the embodiment of FIG. 29 is replaced with a reduced rotational resistance, thereby facilitating insertion of the instrument 30.

Other embodiments of the invention are associated with various structures for mounting the axles 43 and 45 relative to the seal housing 25. In the embodiment of FIG. 39, these axles 43 and 45 are mounted on supports 198 and 201 which are in turn pivotally supported by the seal housing 25. The supports 198 and 201 can be spring biased to move the rollers 38 and 41, respectively, toward each other. This bias will facilitate formation of both the zero seal 76 and instrument seal 78.

Figure 40:
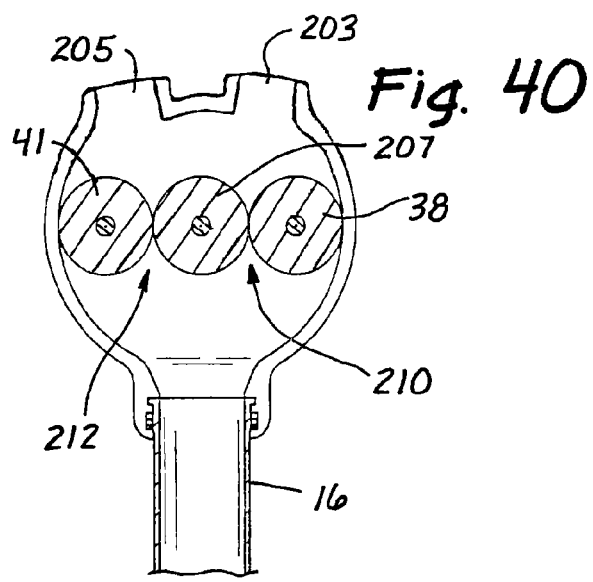
FIG. 40 is an axial cross-section view similar to FIG. 3 and including three rollers defining two working channels.

Two entry ports, 203 and 205, are provided in the embodiment of FIG. 40 which also includes a third roller 207 disposed between the rollers 38 and 41. With this structure, two valves 210 and 212 are formed, one between the rollers 38 and 207 and the other between the rollers 41 and 207. In the absence of any instrument 30, the valves 210 and 212 will form zero seals across the associated ports 203 and 205. When an instrument is inserted into the entry port 203, an instrument seal will be formed by the valve 210. Similarly, an instrument inserted into the entry port 205 will form an instrument seal with the valve 212. Of course rotation of the valves 38, 41 and 207 will vary greatly depending on the timing of instrument introduction and removal.

Figure 41:
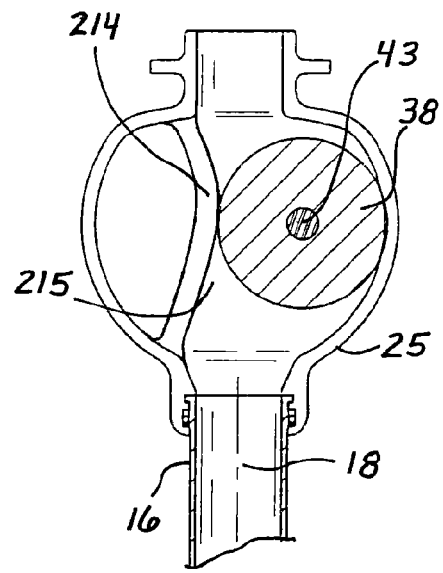
FIG. 41 is an axial cross-section view similar to FIG. 3 wherein a single roller forms a zero seal with a wall of the housing.

The embodiment of FIG. 41 is interesting as it illustrates that only the single roller 38 may be required to form both the zero seal 76 and instrument seal 78. In the illustrated embodiment, an interior wall 214 extends inwardly from the seal housing 25 toward the axis 18 and forms a sealing valve 216 with the roller 38. Thus, the sealing valve 216 forms the zero seal 76 between the wall 214 and the roller 38 in the absence of the instrument 30. When the instrument 30 is inserted, the instrument seal 78 is formed between the wall 214 and the roller 38.

Figure 42:
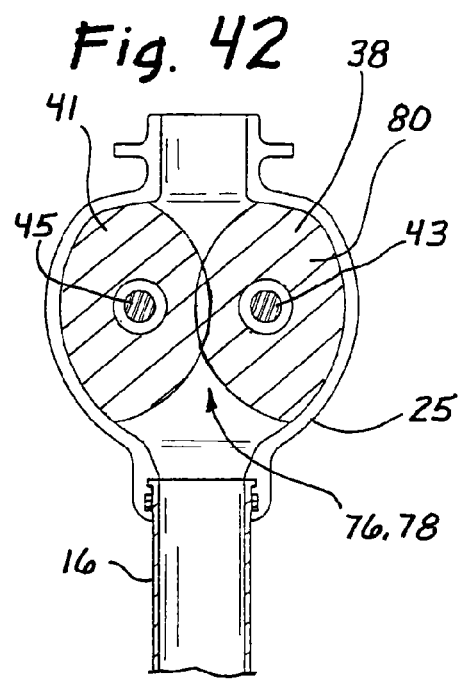
FIG. 42 is an axial cross-section view similar to FIG. 3 wherein the seals in the housing are formed by non-rotatable elements.

In FIG. 42, a sealing valve is formed between the rollers 38 and 41 as in previous embodiments. Although these rollers 38 and 41 are formed on the axles 43 and 45, respectively, they do not rotate, but rather have a fixed relationship with the seal housing 25. This structure is representative of many embodiments wherein the gel material 80 forms both the zero seal 76 and instrument seal 78 but without the rolling characteristics associated with previous embodiments.

Figure 43:
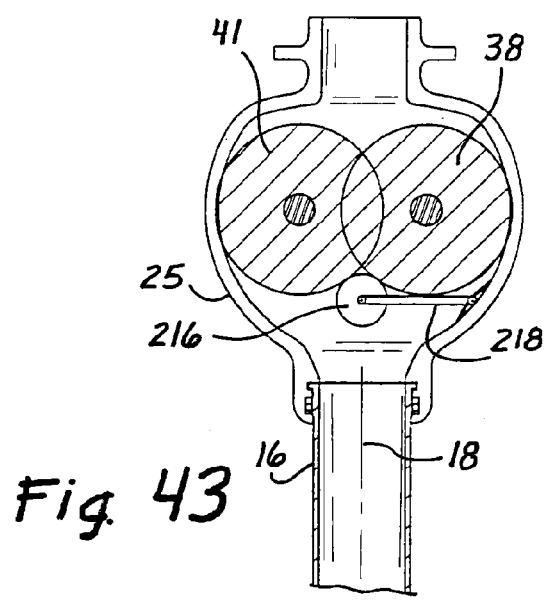
FIG. 43 is an axial cross-section view similar to FIG. 3 wherein the zero seal in the housing is facilitated with a spring-biased roller.

The embodiment of FIG. 43 is similar to that of FIG. 3 in that it includes the two rollers 38 and 41 which were disposed in the seal housing 25. In this embodiment, however, formation of the zero seal 76 is facilitated with the addition of a third roller 216 which is supported on an arm 218 pivotally mounted on the seal housing 25. This roller 216 is operatively disposed distally of and in contact with the rollers 38 and 41. In this position, the roller 216 forms a zero seal with each of the rollers 38 and 41 in the absence of the instrument 30. When the instrument 30 is inserted, the instrument seal 78 is initially formed with the rollers 38 and 41. However, as the instrument 30 is inserted further, it contacts the roller 216 and pivots it away from the axis 18. In this position, the roller 216 performs no sealing function. However, when the instrument 30 is removed, the arm 218 is biased to move back to the operative position to facilitate formation of the zero seal 76.

A similar embodiment is illustrated in FIG. 44 wherein the roller 216 is sufficiently large to form the zero seal 76 with a pair of interior walls 221 and 223 which helped define the working channel 27. In this case, however, a septum 225 is provided to form the instrument seal 78. As the instrument 30 is inserted into the working channel 27, the instrument seal 78 is formed with the septum 225. As the instrument 30 is further inserted, it contacts the roller 216 and pivots the biased arm 218 away from the working channel 27. As the instrument 30 is removed, the zero seal 76 is established and the instrument seal 78 is broken. Note that with the same cross-sectional view illustrated in FIG. 44, the interior walls 221 and 223 may comprise a single cylindrical wall. In such an embodiment, the roller 216 preferably has a spiral configuration. Alternatively, the walls 221 and 223 may each have planar configurations in which case the roller 216 is preferably cylindrical in shape.

In the embodiment of FIG. 45, the zero seal is formed by two rollers, specifically the roller 216 carried by the biased arm 218, and a second roller 227 carried by a biased arm 230. In this embodiment, the roller 216 forms a seal with the interior wall 221 while the roller 227 forms a seal with the interior wall 223. A further seal 232 is required in this embodiment between the roller 216 and 227. In this embodiment, the two wall seals and the further seal 232 combine to form the zero seal 76 in the absence of the instrument 30. As in the previous embodiment, the instrument seal 78 is formed by the septum 225.

The embodiment of FIG. 46 is similar to that of FIG. 3 in that it includes the two rollers 38 and 41. However in this case, a pair of levers 231 and 232 are individually pivotal on the housing 25 and biased into contact with the associated roller 38 and 41, respectively. With the levers 231 and 232, extending inwardly of the housing 25 and toward each other, they are maintained generally in a closed position illustrated in FIG. 46 but movable to an open position upon insertion of the instrument 30. With these operating characteristics, the leverage 231 and 232 can aid several advantages to the present embodiment. In the closed state, the levers 231 and 232 form pockets 233 which can be used in the manner previously disclosed. As the instrument 30 is inserted, the levers 231 and 232 help guide it toward the intersection of the rollers 38 and 41. If the instrument 30 has a sharp point, the levers 231 and 232 will ensure that this point does not engage the rollers 38 and 41 at a sharp angle. Rather, the sharp point of the instrument will contact the rollers 38 and 41 only at a small acute angle facilitating rotation of the rollers 38 and 41 and thereby inhibiting any damage to the gel material 80.

FIG. 47 illustrates an embodiment wherein the working channel 27 is lined with a tubular braid or mesh 234, at least within the seal housing 25.

Accordingly, the mesh 234 extends between the rollers 38 and 41 and greatly facilitates introduction of the instrument 30 centrally through the housing 25. In the absence of the instrument 30, the gel forming material 80 forming the rollers 38 and 41 is sufficiently compliant to form the zero seal even with the mesh 234 present between the rollers 38, 41. When the instrument 30 is inserted, the gel material 80 forms the instrument seal 70 with the braid 234 and the instrument 30. When the mesh 234 is made from a low-friction material, such as polyester, it not only guides the instrument 30 centrally along the working channel 27, but also reduces the insertion forces encountered by the instrument 30.

Similarly braid material can also be used to form covers 236 and 238 on the respective rollers 38 and 41 as shown in FIG. 48. Once again, it will be noted that the compliance of the gel material 38 is sufficient to form both the zero seal 76 and the instrument seal 78, notwithstanding the presence of the mesh 236, 238 between the rollers 38, 41.

The embodiment of FIG. 49 illustrates the seal housing 25 with the rollers 38 and 41 disposed inside. In this case, the rollers 38, 41 are sized and configured to respond to distal pressure by moving proximally within the housing 25 to a proximal position as illustrated in FIG. 49. In this proximal position, the lateral seals 63 and 65 are formed between the housing 25 and the rollers 38 and 41, respectively. These seals, together with a further seal 241 formed between the rollers 48 and 41 complete the zero seal 76. As the instrument 30 is inserted, the free-floating rollers 38 and 41 are moved distally by the instrument breaking the zero seal 76 but at the same time forming the instrument seal 78 with the instrument 30. This distal movement of the rollers 38 and 41 is accomplished with the distal force of the instrument 30 which acts against the proximal force of any distal pressure.

With respect to the embodiment of FIG. 49, it is contemplated that the instrument 30 may be a pressurized injectate introduced into the working channel 27. To the extent that the pressure of the injectate on the proximal side of the rollers 38, 41 exceeds the fluid pressure on the distal side of the rollers 38, 41, the pressure differential will cause the rollers 38, 41 to move distally, thereby creating a gap 243 through which the injectate can pass between the rollers 38 and 41 as shown in FIG. 50.

Note that a pressure on a proximal side of the rollers 38, 41 has the opposite effect. To the extent that the pressure on the distal side of the rollers 38, 41 exceeds the pressure on the proximal side of the rollers 38, 41, the pressure differential will cause the rollers 38, 41 to move proximally into a more confined space, thereby creating a seal to inhibit proximal flow. Thus, with this embodiment, the device functions as a one-way valve.

In another embodiment illustrated in FIG. 51, the rollers 38 and 41 are included in a roller assembly 244 which is carried by a catheter shaft 245 and moved within a body conduit 247. The rollers 38, 41 are retained within a rigid housing 250 in an orientation that is generally perpendicular to the length of the shaft 245 and the conduit 247. A balloon 252 is disposed around the housing 250 in order to reduce any trauma to the body conduit 247. With this configuration, the gel rollers 38, 41 and the balloon 252 seal the conduit 247 on either side of the roller assembly 244. Distal pressures from gases, liquids or solids can facilitate an opening between the rollers 38 and 41 thereby permitting passage to the proximate side of the roller assembly 244.

The embodiment of FIG. 51 would also facilitate insufflation of the conduit 247 distal of the roller assembly 245, while permitting passage of instrumentation into the insufflated conduit 247 without any loss of gases or fluids.

Another embodiment, illustrated in FIG. 52 is also adapted for use within the body conduit 247. In this case, the rollers 38 and 41 are rotationally mounted on legs 253, which extend from the catheter shaft 245. In the absence of any exterior housing, such as that designated by the reference numeral 250 in FIG. 50, the gel rollers 38, 41 are free to contact the conduit 247. Seals formed between the rollers 38 and 41 can function in the matter previously discussed.

It is also contemplated that the rollers 38 and 41 can be disposed in a transverse orientation within a lumen 254 of a tubular shaft 257 as illustrated in FIG. 53. In this case, the rollers 38 and 41 would be mounted on the axles 43 and 45, respectively, which are in turn carried by the shaft 257. With this construction, the rollers 38 and 41 form the zero seal 76 across the lumen 254 of the shaft 257 but also accommodate introduction of an instrument, such as a suture 256, along the lumen 254

Figure 55:
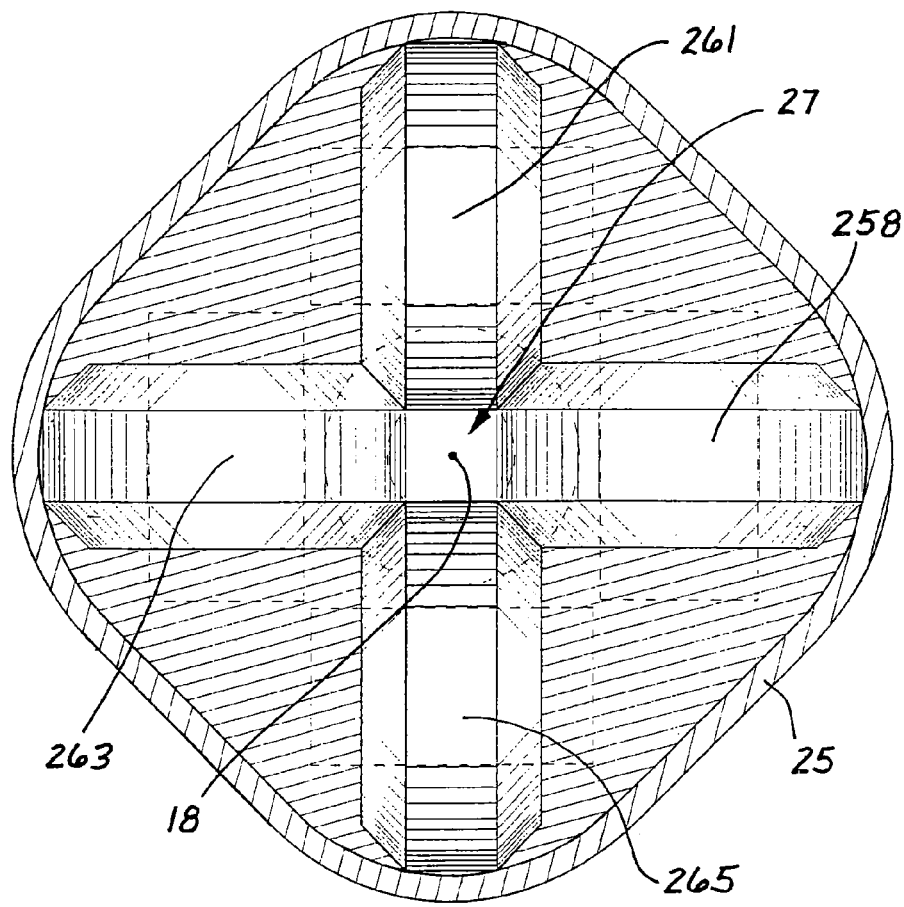
Figure 56:
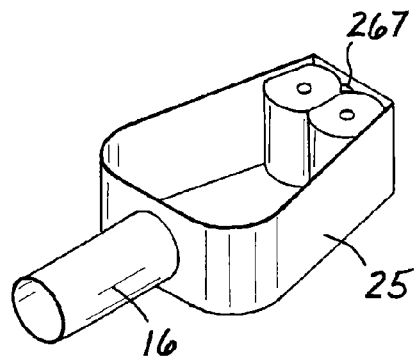
FIG. 56 is a perspective view of an embodiment wherein the seal housing has a triangular or trapezoidal configuration with a narrow proximal end and a wide distal end.

The embodiment of FIG. 54 is most easily distinguished with reference to the cross-sectional view of FIG. 55. In this embodiment, the seal mechanism within the seal housing 25 includes four rollers 258, 261, 263, 265, with the rollers 258 and 263 mounted parallel to each other. The rollers 261 and 265 are mounted parallel to each other and angularly spaced by 90 degrees from the rollers 258 and 263. The four rollers 258-265 are formed of the gel material 80 in a preferred embodiment and contact each of the two adjacent rollers along the working channel 27. Thus the rollers 258-265 can be disposed generally radially of the axis 18. With this configuration, the relatively narrow rollers 258-265 can form seals with each other and thereby facilitate formation of both the zero seals 76 and instrument seals 78.

A further embodiment of the invention is illustrated in FIGS. 56-61. This is the same embodiment illustrated in multiple stages of operation with different sizes of instruments. For example, the perspective view of FIG. 56 and the top plan view of FIG. 59 illustrated this embodiment in the absence of the instrument 30. In this case, the embodiment includes the cannula 16 and the seal housing 25 having a proximal opening 267 for receipt of the instrument 30. The seal housing 25 has a generally triangular or trapezoidal configuration with a relatively narrow proximal end 269, and a relatively wide distal end 270. The rollers 38 and 41 are mounted on post 272 and 274, respectively, which are fixed to the walls of the housing 25 at the proximal end 269. When the rollers 38 and 41 are disposed at the proximal end 269, the gel material 80 tends to form the rollers 38, 41, concentrically around the post 272 and 274, respectively.

Figure 57:
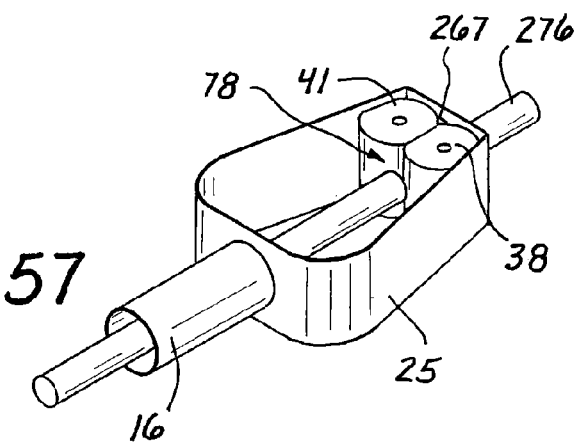
FIG. 57 is a perspective view similar to FIG. 56 showing seal elements at the proximal end of the housing in response to insertion of a small instrument.

As perhaps best illustrated in FIG. 59, the rollers 38 and 41 in this normal position not only form seals with the housing 25, but also form the zero seal 76 with each other. When a relatively small instrument, such as that designated by the reference numeral 276 in FIGS. 57 and 60, is introduced through the opening 267, it tends to separate the rollers 38 and 41 sufficiently to permit passage of the instrument. If the instrument 276 is sufficiently small, the instrument seal 78 will be formed around the instrument 276 while it is still in the proximal position.

Figure 58:
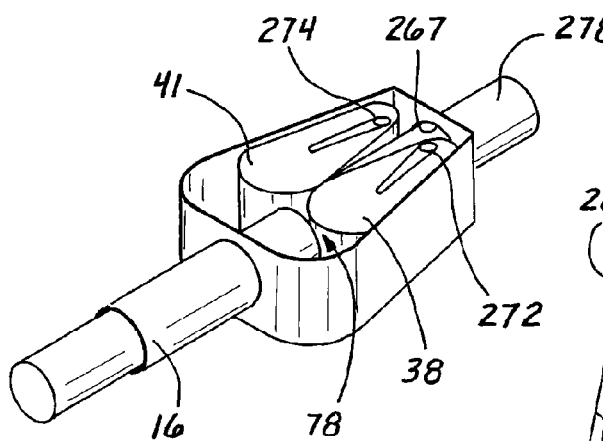
FIG. 58 is a perspective view similar to FIG. 57 illustrating the seal elements stretched toward a distal end of the housing in response to insertion of a large instrument.

For comparison, a larger instrument, designated by the reference numeral 278 in FIGS. 58 and 61 can also be accommodated by this embodiment. In this case, the larger instrument 276 cannot be accommodated by the rollers 38 and 41 in the proximal position. As a result, the instrument 278 forces the rollers 38 and 41 to translate distally toward the wider distal end 270 of the seal housing 25. With the additional width provided by the housing 25, the gel material 80 of the rollers 38 and 41 can stretch on the post 272 and 274 respectively to accommodate the larger instrument 278. In this stretch configuration, the rollers 38, 41 form the instrument seal 78 with the larger instrument 278.

Figure 62:
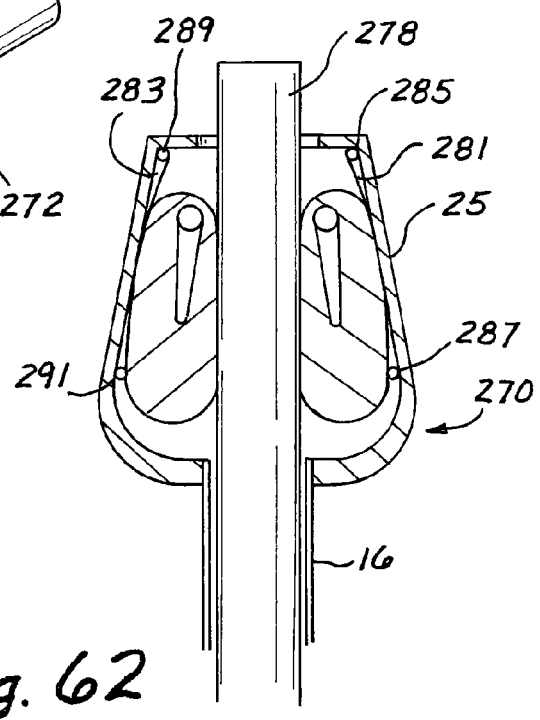
FIG. 62 is a top plan view similar to FIG. 59 and illustrating rolling endless loops of low-friction material disposed between the seal elements and the sidewalls of the housing.

The stretching or translation of the rollers 38 and 41 can be facilitated by providing a low friction surface between the rollers 38, 41 and the housing 25. In a preferred embodiment illustrated in FIG. 62, two endless loops, 281 and 283, are formed of a low-friction material such as polytetrafluoroethylene. The loop 281 is mounted between posts 283 and 285 which are fixed to the housing 25. With this structure, the loop 281 is disposed between the roller 38 and the housing 25. Similarly, the loop 283 is mounted to extend between posts 289 and 291 between the roller 41 and the housing 25. As the larger instrument 278 is inserted, the rollers 38 and 41 translate toward the wider distal end 270 in the manner previously discussed. However, with the embodiment of FIG. 66, the low-friction loops 281 and 283 significantly reduce frictional forces between the rollers 38 and 41 and the housing 25. This, of course, reduces the insertion forces associated with the larger instrument 278.

From the foregoing embodiments, it would be apparent that the concept of the present invention may vary widely depending on the particular quality, characteristics and advantages desired for a given embodiment. For the most part, the concept will include at least one roller disposed within the seal housing of a trocar. The roller may not rotate, but in most embodiments will either translate or rotate relative to the seal housing. The roller will typically define at least a portion of the working channel of the trocar and may operate relative to a wall or another roller. The roller may be stationary or it may rotate relative to a fixed or rotatable axle. Rotation of the roller will typically reduce insertion forces and protect the material of the roller. Braids, levers, and fixed walls can aid in defining the working channel. Multiple rollers may be used to define more than one working channel. Idler rollers and wiper seals can be used to find pockets for the receipt of lubricants or antiseptic materials, for example. The rollers will typically have a high level of compliance so that instrument seals can be formed over a large range of instrument diameters. Inflatable rollers are contemplated but typically this compliance will be provided by a gel material offering a high degree of stretchability.

Due to the wide variation in embodiments included in this concept, one is cautioned not to limit the concept only to the embodiments disclosed, but to determine the scope of the invention only with reference to the following claims.

What is claimed is:

1. A surgical access device comprising:
   a seal housing;
   a working channel extending longitudinally through the seal housing;
   at least one axle disposed in the seal housing and spaced from the working channel; and
   at least one roller mounted on and rotatable about the at least one axle and in the presence of an instrument in the working channel defines an instrument seal;
   wherein the at least one roller is rotatable only about the at least one axle and is only translatable proximally and distally, and wherein the at least one roller is configured to be in direct contact with the instrument in the working channel to provide the instrument seal and in the absence of the instrument in the working channel, defines a zero seal in the working channel.

2. The surgical access device of claim 1 wherein the seal housing has a low friction coating in contact with the at least one roller.

3. The surgical access device of claim 1 further comprising a low friction material disposed between the at least one roller and the seal housing.

4. The surgical access device of claim 1 wherein the seal housing has a first recess and a second recess disposed within an inner surface of the seal housing and the seal housing having an inwardly extending protrusion disposed between the first and second recesses.

5. The surgical access device of claim 1 wherein the seal housing comprises two entry ports and one exit port.

6. The surgical access device of claim 1 further comprising a lever pivotably connected to the seal housing and biased to contact the at least one roller.

7. A surgical access device comprising:
   a seal housing;
   a working channel extending longitudinally through the seal housing;
   at least one axle disposed in the seal housing and spaced from the working channel; and
   at least one roller mounted on and rotatable about the at least one axle and in the presence of an instrument in the working channel defines an instrument seal, and wherein the at least one roller is configured to be in direct contact with the instrument in the working channel to provide the instrument seal and in the absence of the instrument in the working channel, defines a zero seal in the working channel;
   wherein the seal housing has an oblong recess with a length parallel to the working channel and a width perpendicular to the working channel, the length of the oblong recess being greater than the width of the oblong recess and wherein the at least one axle is disposed in the oblong recess and the at least one axle is biased towards a proximal end of the oblong recess.

8. A surgical access device comprising:
   a seal housing;
   a working channel extending longitudinally through the seal housing;
   at least one axle disposed in the seal housing and spaced from the working channel; and
   at least one roller mounted on and rotatable about the at least one axle and in the presence of an instrument in the working channel defines an instrument seal;
   wherein the at least one axle comprises a first axle and a second axle and the at least one roller comprises a first roller, the first roller being mounted on and rotatable about the first and second axles, and wherein the first and second rollers are configured to be in direct contact with the instrument in the working channel to provide the instrument seal and in the absence of the instrument in the working channel, define a zero seal in the working channel.

9. A surgical access device comprising:
   a seal housing;
   a working channel extending longitudinally through the seal housing;
   at least one axle disposed in the seal housing and spaced from the working channel; and
   at least one roller mounted on and rotatable about the at least one axle and in the presence of an instrument in the working channel defines an instrument seal, and wherein the at least one roller is configured to be in direct contact with the instrument in the working channel to provide the instrument seal and in the absence of the instrument in the working channel, defines a zero seal in the working channel;

wherein the at least one axle has an oblong shape.

10. A surgical access device comprising:

a seal housing;

a working channel extending longitudinally through the seal housing;

at least one axle disposed in the seal housing and spaced from the working channel; and at least one roller mounted on and rotatable about the at least one axle and in the presence of an instrument in the working channel defines an instrument seal, and wherein the at least one roller is configured to be in direct contact with the instrument in the working channel to provide the instrument seal and in the absence of the instrument in the working channel, defines a zero seal in the working channel;

wherein the at least one axle is deformable along a length of the at least one axle.

11. The surgical access device of claim 10 wherein the at least one axle comprises a spring.

12. A surgical access device comprising:

a seal housing;

a working channel extending longitudinally through the seal housing;

at least one axle disposed in the seal housing and spaced from the working channel; and at least one non-pivotable roller mounted on and rotatable about the at least one axle and in the presence of an instrument in the working channel defines an instrument seal, and wherein the at least one roller is configured to be in direct contact with the instrument in the working channel to provide the instrument seal and in the absence of the instrument in the working channel, defines a zero seal in the working channel;

wherein the at least one roller being made of gel material, wherein the gel material of the at least one roller includes at least one groove beginning at an outer surface of the gel material and extends inwardly towards the at least one axle.

13. The surgical access device of claim 12 wherein the at least one axle has a non-cylindrical shape and the gel material of the at least one roller conforms to the non-cylindrical shape of the at least one axle.

14. The surgical access device of claim 12 wherein the at least one axle is formed of a rigid plastic and the gel material is molded to the at least one axle.

15. The surgical access device of claim 12 wherein the gel material of the at least one roller includes at least one void between an outer surface of the gel material and the at least one axle.

16. A surgical access device comprising:

a seal housing;

a working channel extending longitudinally through the seal housing;

at least one axle disposed in the seal housing and spaced from the working channel; and at least one non-pivotable roller mounted on and rotatable about the at least one axle and in the presence of an instrument in the working channel defines an instrument seal, and wherein the at least one roller is configured to be in direct contact with the instrument in the working channel to provide the instrument seal and in the absence of the instrument in the working channel, defines a zero seal in the working channel;

wherein the at least one roller being made of gel material, wherein the gel material of the at least one roller has an outer surface defined by alternating peaks and valleys.

17. A surgical access device comprising:

a seal housing;

a working channel extending longitudinally through the seal housing;

at least one axle disposed in the seal housing and spaced from the working channel; and at least one non-pivotable roller mounted on and rotatable about the at least one axle and in the presence of an instrument in the working channel defines an instrument seal, and in the absence of the instrument in the working channel, defines a zero seal in the working channel;

wherein the at least one roller being made of gel material, wherein the at least one roller comprises a first roller and a second roller and further comprising a tubular mesh extending between the first and second rollers.

* * * * *